United States Patent [19]
Sledziewski et al.

[11] Patent Number: 5,618,712
[45] Date of Patent: Apr. 8, 1997

[54] HUMAN LYSOZYME

[75] Inventors: Andrzej Sledziewski; Ewa Chlebowicz-Sledziewska, both of Seattle, Wash.; Peter Swetly, Vienna, Austria; Gunther Adolf, Vienna, Austria; Rudolf Hauptmann, Vienna, Austria; Maria J. Castanon, Vienna, Austria; Walter Spevak, Stockerau, Austria

[73] Assignee: Boehringer Ingelheim Zentrale GmbH, Germany

[21] Appl. No.: 225,280

[22] Filed: Apr. 4, 1994

Related U.S. Application Data

[63] Continuation of Ser. No. 61,346, May 17, 1993, abandoned, which is a continuation of Ser. No. 545,129, Jun. 27, 1990, abandoned, which is a continuation of Ser. No. 929,582, Nov. 12, 1986, abandoned.

[30] Foreign Application Priority Data

Nov. 12, 1985 [DE] Germany .......................... 35 40 075.7

[51] Int. Cl.[6] .............................. C12N 15/56; C12N 9/36; C12N 15/70; C12N 15/81
[52] U.S. Cl. ..................... 435/206; 435/69.1; 435/252.3; 435/254.21; 435/320.1; 536/23.2; 935/14; 935/28; 935/29; 935/69; 935/73
[58] Field of Search .................................. 435/206, 69.1, 435/69.6, 252.3, 252.33, 254.2, 320.1, 23.2

[56] References Cited

U.S. PATENT DOCUMENTS

| | | | |
|---|---|---|---|
| 4,546,082 | 10/1985 | Kurjan et al. | 435/172.3 |
| 4,757,006 | 7/1988 | Toole, Jr. | 435/70 |
| 4,766,068 | 8/1988 | Oeda et al. | 435/69.1 |
| 4,945,051 | 7/1990 | Kikuchi et al. | 435/172.3 |

FOREIGN PATENT DOCUMENTS

| | | |
|---|---|---|
| 901223 | 3/1985 | Belgium . |
| 0123544 | 4/1983 | European Pat. Off. . |
| 0129073 | 5/1983 | European Pat. Off. . |
| 0155189 | 3/1984 | European Pat. Off. . |
| 0181634 | 11/1984 | European Pat. Off. . |
| 0208472 | 6/1985 | European Pat. Off. . |

OTHER PUBLICATIONS

Gubler et al., *Gene* 25: 263–269 (1983).
Muraki et al. *Agric Biol. Chem.* 49(9): 2829–2831 (1985).
Sipple et al., *Nucleic Acid Research* 5 (9): 3275–3294 (1978).
Land et al., *Methods Enzymol.* 100: 285–292 (1983).
Vasavada et al., *Gene* 34: 9–15 (1985).
Chung, L.P. et al., Cloning the human lysozyme cDNA: Inverted Alu repeat in the mRNA an in situ hybridization for macrophages and Paneth cells, *Proc. Natl. Acad. Sci USA* 85:6227–6231 (Sep. 1988).

(List continued on next page.)

*Primary Examiner*—Robert A. Wax
*Assistant Examiner*—William W. Moore
*Attorney, Agent, or Firm*—Sterne, Kessler, Goldstein & Fox P.L.L.C.

[57] ABSTRACT

This invention relates to a process for preparing human lysozyme and the human lysozyme protein itself.

46 Claims, 16 Drawing Sheets

```
         10        20        30        40        50        60
CCCCCCCCCCCCCCCCCCCATTGTTCTGGGGCTTGTCCTCCTTTCTGTTACGGTTCAAGG 70        80        90       100       110       120
CAAGGTCTTTGAAAGGTGTGAGTTGGCCAGAACTCTGAAAAGATTGGGAATGGATGGCTA 130       140       150       160       170       180
CAGGGGAATCAGCCTAGCAAACTGGATGTGTTTGGCCAAATGGGAGAGTGGTTACAACAC 190       200       210       220       230       240
ACGAGCTACAAACTACAATGCTGGAGACAGAAGCACTGATTATGGGATATTTCAGATCAA 250       260       270       280       290       300
TAGCCGCTACTGGTGTAATGATGGCAAAACCCCAGGAGCAGTTAATGCCTGTCATTTATC 310       320       330       340       350       360
CTGCAGTGCTTTGCTGCAAGATAACATCGCTGATGCTGTAGCTTGTGCAAAGAGGGTTGT 370       380       390       400       410       420
CCGTGATCCACAAGGCATTAGAGCATGGGTGGCATGGAGAAATCGTTGTCAAAACAGAGA 430       440       450       460       470       480
TGTCCGTCAGTATGTTCAAGGTTGTGGAGTGTAACTCCAGAATTTTGGGGGGGGGGGGG

490
GGGGGGGGG
```

OTHER PUBLICATIONS

Ikehara, M., et al., Synthesis of a Gene Coding for Human Lysozyme, *Chem. Pharm. Bull.* 34(5):2202–2208 (1986).

Jollés, P. et al., What's new in lysozyme research?, *Molecular and Cellular Biochemistry* 63:165–189 (1984).

Matthews, B.W. et al., Common precursor of lysozymes of hen egg–white and bacteriophage T4, *Nature* 290:334–335 (Mar. 26, 1981).

Sambrook, J. et al., *Molecular Cloning: A Laboratory Manual*, Second Edition, Cold Spring Harbor Laboratory Press, p. 11.14 (1989).

Qasba, P.K. et al., Similarity of the nucleotide sequences of rat alpha–lactalbumin and chicken lysozyme genes, *Nature* 308:377–380 (Mar. 22, 1984).

Woods, D., Oligonucleotide Screening of cDNA Libraries, *Focus* 6(3):1–3 (Jul. 1984).

Yoshimura, K. et al., Human Lysozyme: Sequencing Of A cDNA, And Expression And Secretion By *Saccharomyces Cerevisiae, Biochemical and Biophysical Research Communications* 150(2) :794–801 (Jan. 29, 1988).

Castañon et al., *Gene* 66:223–234 (1988).

Muraki et al., *Agric. Biol. Chem.* 50(3):713–723 (1986).

Gubler, U., et al., "A Simple and Very Efficient Method for Generating cDNA Libraries," *Agric. Biol. Chem.* 49(9):2829–2831 (1985).

Sippel, A.E., et al., "Cloning of Chicken Lysozyme Structural Gene Sequences Synthesized in Vitro," *Nucleic Acid Research* 5(9):3275–3294 (1978).

Stent, G.S. and Calendar, R., in *Molecular Genetics, An Introductory Narrative*, 2nd Edition, 1978, pp. 547–550.

Maniatis, T., et al., Eds., 1982, in *Molecular Cloning*, A Laboratory Manual, pp. 218–219, Cold Spring Harbor Laboratory Press.

Maniatis et al. Molecular Cloning –A Laboratory Manual. (1982) pp. 226–227.

Powwels Expression Vectors VIII–B–h–i–ll (1985). Elseivier Science, Publisher.

Hitzeman et al Science. 219 (1983) pp. 620–625.

Jaye, M., et al., 1983, Nucleic Acids Research, 11(8): 2325–2335.

Ullrich, A., et al., 1984, The EMBO Journal, 3(2): 361–364.

Sundström, Ch., et al., 1976, International Journal of Cancer 117:565–577.

Brake, A.J., et al., 1984, Proc. Nat'l. Acad. Sci. USA 81: 4642–4646.

Ammerer, G., 1983, Methods in Eazymology 101:192–201.

Russell, D.W., et al, 1983, Journal of Biologicol Chemistry 258(4): 2674–82.

Suggs S.V. et al., 1981, Proceedings, National Academy of Sciences, USA, 78(11): 6613–6617.

Derynck, R., et al., 1984, Cell 38: 287–297.

Lathe, R., 1985, Journal of Molecular Biology 183:1–12.

Jung, A., et al., 1980, Proceedings of the National Academy of Sciences, USA, 77(10): 5795–5763.

Fig. 2.
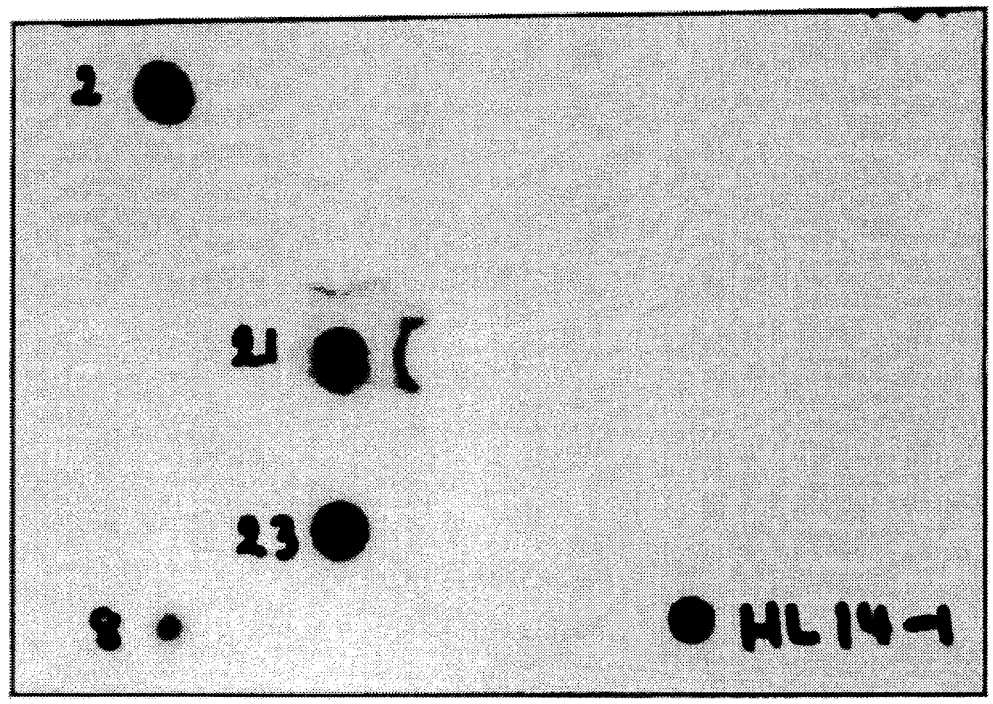
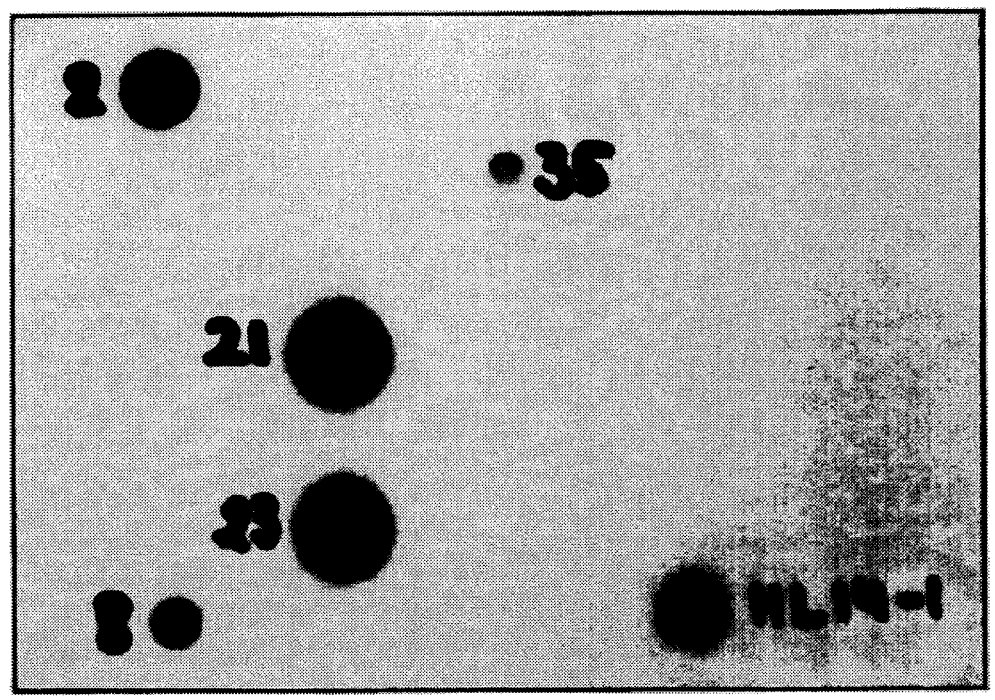

100 bp

```
         10        20        30        40        50        60
CCCCCCCCCCCCCCCCCCCCATTGTTCTGGGGCTTGTCCTCCTTTCTGTTACGGTTCAAGG 70        80        90       100       110       120
CAAGGTCTTTGAAAGGTGTGAGTTGGCCAGAACTCTGAAAAGATTGGGAATGGATGGCTA 130       140       150       160       170       180
CAGGGGAATCAGCCTAGCAAACTGGATGTGTTTGGCCAAATGGGAGAGTGGTTACAACAC 190       200       210       220       230       240
ACGAGCTACAAACTACAATGCTGGAGACAGAAGCACTGATTATGGATATTTCAGATCAA 250       260       270       280       290       300
TAGCCGCTACTGGTGTAATGATGGCAAAACCCCAGGAGCAGTTAATGCCTGTCATTTATC 310       320       330       340       350       360
CTGCAGTGCTTTGCTGCAAGATAACATCGCTGATGCTGTAGCTTGTGCAAAGAGGGTTGT 370       380       390       400       410       420
CCGTGATCCACAAGGCATTAGAGCATGGGTGGCATGGAGAAATCGTTGTCAAAACAGAGA 430       440       450       460       470       480
TGTCCGTCAGTATGTTCAAGGTTGTGGAGTGTAACTCCAGAATTTTGGGGGGGGGGGGG

490
GGGGGGGGGG
```

Fig. 4a

```
                                                              1
                                                        LYS VAL PHE
ILE VAL LEU GLY LEU VAL LEU LEU SER VAL THR VAL GLN GLY LYS VAL PHE 10                               20
GLU ARG CYS GLU LEU ALA ARG THR LEU LYS ARG LEU GLY MET ASP GLY TYR
GLU ARG CYS GLU LEU ALA ARG THR LEU LYS ARG LEU GLY MET ASP GLY TYR

30
ARG GLY ILE SER LEU ALA ASN TRP MET CYS LEU ALA LYS TRP GLU SER GLY
ARG GLY ILE SER LEU ALA ASN TRP MET CYS LEU ALA LYS TRP GLU SER GLY 40                               50
TYR ASN THR ARG ALA THR ASN TYR ASN ALA GLY ASP ARG SER THR ASP TYR
TYR ASN THR ARG ALA THR ASN TYR ASN ALA GLY ASP ARG SER THR ASP TYR 60                               70
GLY ILE PHE GLN ILE ASN SER ARG TYR TRP CYS ASN ASP GLY LYS THR PRO
GLY ILE PHE GLN ILE ASN SER ARG TYR TRP CYS ASN ASP GLY LYS THR PRO

80
GLY ALA VAL ASN ALA CYS HIS LEU SER CYS SER ALA LEU LEU GLN ASP ASN
GLY ALA VAL ASN ALA CYS HIS LEU SER CYS SER ALA LEU LEU GLN ASP ASN 90                              100
ILE ALA ASP ALA VAL ALA CYS ALA LYS ARG VAL VAL ARG ASP PRO GLN GLY
ILE ALA ASP ALA VAL ALA CYS ALA LYS ARG VAL VAL ARG ASP PRO GLN GLY 110                             120
ILE ARG ALA TRP VAL ALA TRP ARG ASN ARG CYS GLN ASN ARG ASP VAL ARG
ILE ARG ALA TRP VAL ALA TRP ARG ASN ARG CYS GLN ASN ARG ASP VAL ARG

130
GLN TYR VAL GLN GLY CYS GLY VAL
GLN TYR VAL GLN GLY CYS GLY VAL Ochre
```

Fig. 5

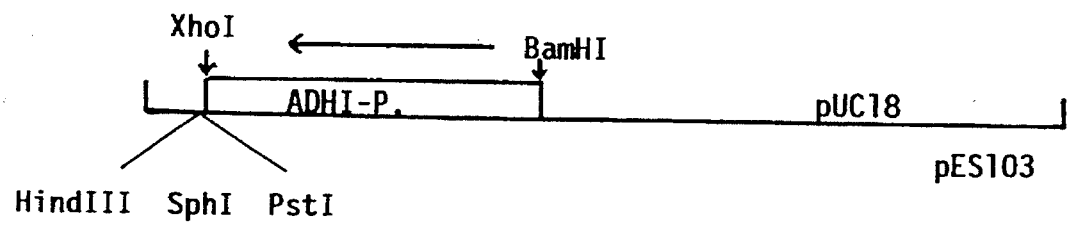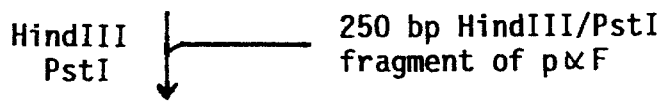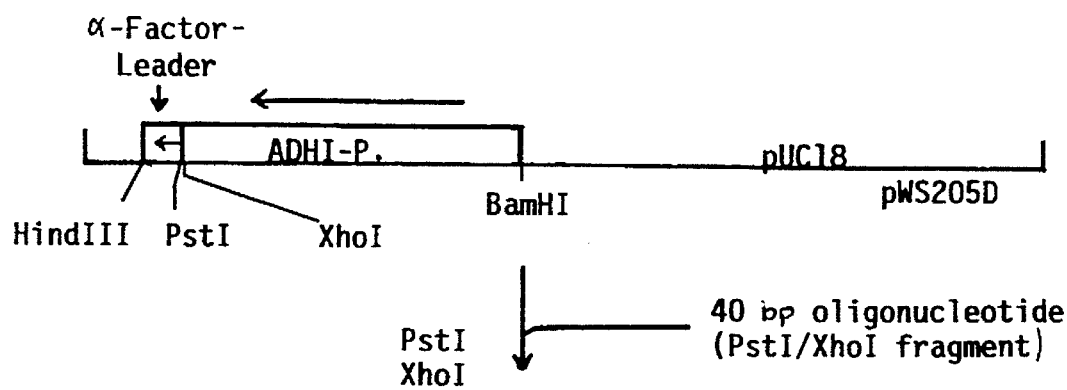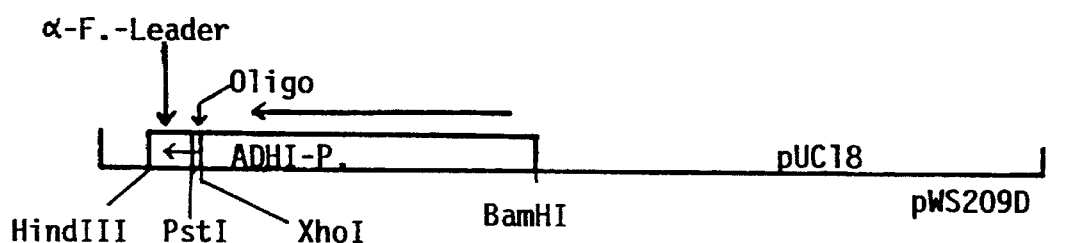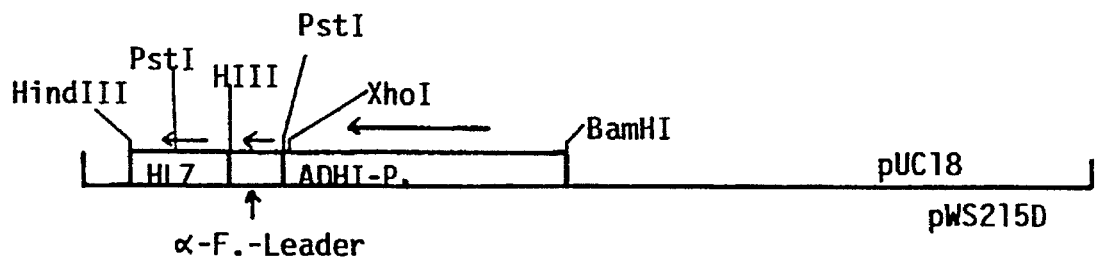
Fig. 7

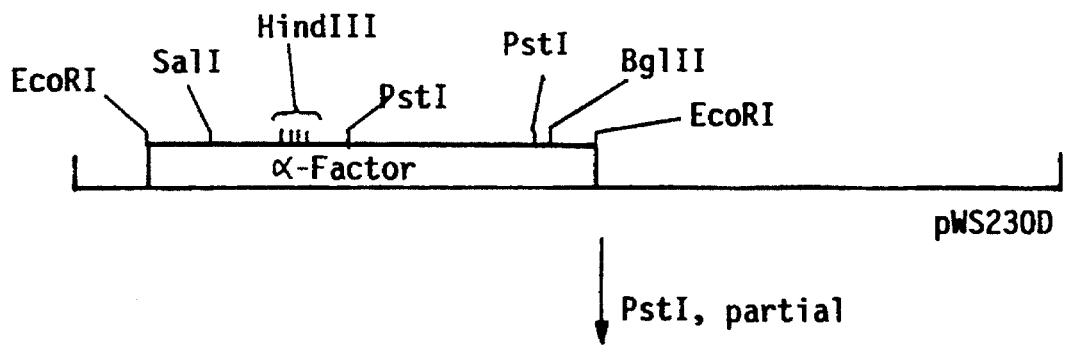
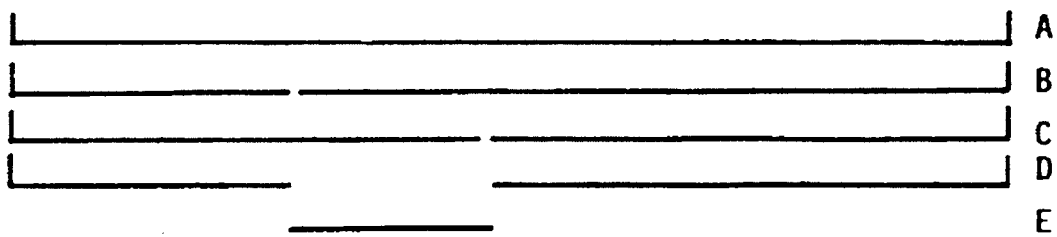
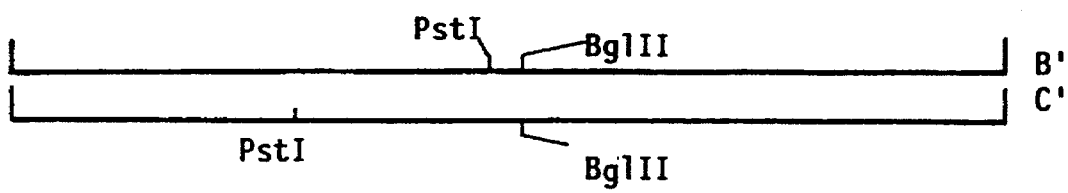
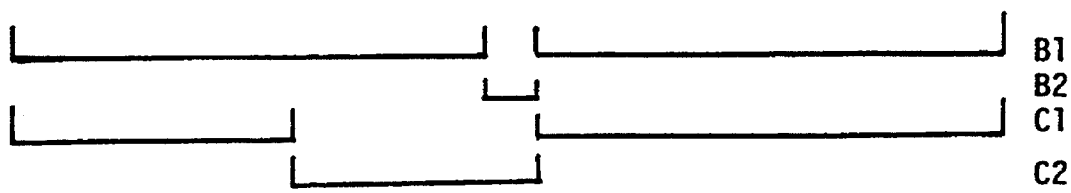
Fig. 14a

HUMAN LYSOZYME

This application is a continuation of application Ser. No. 08/061,346, filed May 17, 1993 now abandoned, which is a continuation of application Ser. No. 07/545,129, filed Jun. 27, 1990, now abandoned, which is a continuation, of application Ser. No. 06/929,582, filed Nov. 12, 1986, now abandoned.

BACKGROUND OF THE INVENTION

1. Field of the Invention

This invention relates to the synthesis and isolation of cDNA coding human lysozyme protein, the preparation of human lysozyme and human lysozyme protein itself. The invention also relates to the possibilities of therapeutic use thereof, as illustrated by way of example in the embodiments which follow. In particular, the invention relates to a bacterium plasmid which contains a cDNA sequence for part of the human lysozyme signal peptide, a cDNA sequence for the entire mature lysozyme protein and, at the 3' end, part of a non-coding sequence of the human lysozyme gene. The invention further relates to expression vectors such as plasmids, with the nucleotide sequences coding for human lysozyme as inserts and various host organisms or cultures which permit the preparation of human lysozyme.

2. Brief description of Background Information

Lysozymes are defined as 1,4-beta-N-acetylmuramidases which cleave the glycoside bond between the C-1 of N-acetyl-muramic acid (MurNAc) and the C-4 of N-acetylglucosamine (GlcNAc) in the peptidoglycan of bacteria (1). Alexander Fleming discovered in 1922 that various tissues and secretions as well as hen egg white were capable of lysing some gram positive bacteria. He called the lytic factor a lysozyme, i.e. an enzyme which is capable of lysing bacteria. Fleming showed that lysozyme occurs in homogenised tissue from cartilage and stomach, in tears, saliva, sputum, nasal secretions, pathological urine, serum and in leucocytes, but not in healthy urine, in the cerebrospinal fluid or in sweat (2). The activity of the lysozyme as an anti-bacterial agent appears to be based on both its direct bacteriolytic activity and also on stimulatory effects in connection with phagocytosis of macrophages (3,4).

The important role of lysozyme as a mediator in warding off microbes by means of alveolar macrophages has been demonstrated in the rat: in intact bacteria there is no phagocytosis, whereas lysozyme-damaged bacteria are rapidly phagocytosed (3). Similarly it has been shown that lysozyme can directly enhance the phagocytotic activity of polymorphonuclear leucocytes (5) and macrophages (4). Investigations have been carried out into the effect of lysozyme on microorganisms in the mouth, on seven serotypes of *Streptococcus mutans, Veillonella alcalescens* and virulent and non-virulent strains of *Actinomyces viscosus* T 14. The results showed that various mechanisms could be responsible for the bacteriostatic, lytic and bacteriocidal properties and that the enzyme is not only a selective factor but also an effective factor against microorganisms of the mouth (6). Other postulated functions of lysozyme include immune stimulation (7) and immunological and non-immunological monitoring of host membranes for any neoplastic transformation (8). Determination of the lysozymes from serum and/or urine is used to diagnose various diseases or as an indicator for their development. In acute lymphoblastic leukaemia the lysozyme serum level is significantly reduced, whereas in chronic myelotic leukaemia and in acute monoblastic and myelomonocytic leukaemia the lysozyme concentration in the serum is greatly increased (9,10).

The therapeutically effective use of lysozyme is possible in the treatment of various bacterial and virus infections (Zona, Herpes zoster), in colitis, various types of pain, in allergies, inflammation and in paediatrics (the conversion of cows milk into a form suitable for infants by the addition of lysozyme).

Lysozyme is able to interact with other biologically active proteins in such a way that they develop their full activity (Adinolfi, In: Lampert, Woods (eds), Academic Press, London, 1981, 19–47). Such components may be, for example, complement, lactotransferrin which inhibits the replication of certain microorganisms by forming iron-chelate complexes and antibodies such as sIgA in milk, which potentiates the antibacterial activity of lactotransferrin (Spik et al. Bull. Eur. Physiopath. Resp. 19, 123–130, 1983). Lysozyme, lactotransferrin and immunoglobulins also coexist in various natural secretions such as saliva, tears, various types of milk (Jorieux et al. Protides of the biological Fluids, Proc. 31st Coll. 1984), in the bronchial mucus membrane and in egg white. Lysozyme may additionally be used to advantage to alleviate rheumatic fever and rheumatic pain and has a therapeutic activity in diseases of the rheumatic or arthritic type (Third Int. Symp. on Flemings lysozyme, Milan 1964). Later, lysozyme was also credited with analgesic properties (Bianchi, Eur. J. Pharmacol. 71, 211–221, 1981). More recently, lysozyme was found to have an antinociceptive activity (Bianchi, Clin. Exp. Pharmacol. Physiol. 10, 45–52, 1983). This broad range of activities of lysozyme demonstrates a correspondingly large spectrum for therapeutic use, which means that it is of considerable economic importance.

In all the pharmaceutical applications of lysozyme enumerated here, human lysozyme (HLZ) is preferred to the lysozyme obtained from hen egg white since undesirable side effects of an anaphylactic and/or allergic nature are more likely when using lysozymes of a different species and could interfere with therapy.

Up till now, human milk and human placenta have been the only commercial sources for obtaining human lysozyme. However, the availability of these starting materials is very limited and it is obvious that different preparations will be obtained from one batch to the next. There ought to be advantages in using the widely developed industrial microbiology and the recently developed recombinant DNA technology to produce human lysozyme by means of microorganisms.

The gene for hen egg white lysozyme has been isolated (11,12) and the nucleotide sequence of hen egg white lysozyme mRNA and the exons located on the gene together with their flanking regions have been determined (13). Moreover, the nucleotide sequence of the lysozyme gene of bacteriophage T4 has been clarified (14). The amino acid sequence of HLZ (21,22,23) is known, but the nucleotide sequence coding for HLZ which is shown in this invention is not already known. EPA 181 634 describes the expression of human lysozyme in yeast and *Bacillus subtilis*. Apart from the fact that no special yeast terminator and no authentic HLZ gene is used in EPA 181 634, this HLZ DNA sequence has no preliminary DNA sequence coding for a leader peptide in the event of expression in yeast. The HLZ formed cannot therefore be transported from the host, with the result that it is difficult for an exact tertiary structure to be formed by corresponding disulphide bridge formation. There is therefore no description of how authentic HLZ is obtained according to EP-A181 634. Nor does it tell us how the start methionine is to be removed.

SUMMARY OF THE INVENTION

The object on which this invention is based is to use a strategy in order to synthesise and clone a cDNA with the minimal information of the amino acid sequence of HLZ and to use this cDNA to express a biologically active HLZ protein.

The problem was solved by the finding that, using a mRNA as template, it was possible to construct bacterial hybrid plasmids which contain a cDNA coding for HLZ. The HLZ DNA, as part of the bacterial hybrid vector, may come from any HLZ-producing cells of the human body. Examples of suitable cells are placenta cells, leucocytes from people suffering from acute monoblastic and/or myelomonocytic leukaemia, human colon carcinoma cells, the U-937 cell line or other cell lines which produce HLZ. In a preferred embodiment of the invention, U-937 cells (ATCC CRL 1593) from humans are used. The HLZ DNA may be isolated from a gene bank which contains the HLZ gene. In this invention, chromosomal DNA is not preferred since it probably contains, within its coding region introns (for example, the hen egg white lysozyme gene contains 3 introns (13)), which cannot be cut out using yeast. In the present invention, human lysozyme cDNA is preferred.

The mRNA isolated from U-937 cells is a preferred template for the synthesis of human lysozyme cDNA. For synthesising the first strand of the HLZ cDNA, the reaction is started with oligo $(dT)_{18}$ as primer, which preferably pairs with the 3' end of the above mentioned mRNA. The single strand cDNA is further extended in the presence of dNTPs and reverse transcriptase. The single strand cDNA can subsequently be converted into a double strand cDNA by various known methods. In the present invention the Gubler and Hoffmann method is preferred (15). Synthesis of the second cDNA strand from the single strand cDNA was effected by treating the mRNA hybrid with RNaseH and DNA polymerase I in the presence of dNTPs. Using this method, a double strand cDNA is obtained which can be directly cloned as such. The cloning of double strand cDNA in bacterial vectors can be carried out by various known-methods. Double strand cDNA may be cloned directly as a "blunt end" fragment, via a synthetic linker or by the method known as "homopolymer tailing". When cloning HLZ cDNA, the homopolymer tailing method is preferred. In this method, using the terminal transferase, single strands are formed at the 3' end of the HLZ DNA by the addition of nucleotides (preferably dGTP) at their "blunt" or "staggered" ends. In a separate reaction, the bacterial plasmid is linearised with a restriction endonuclease (when cloning HLZ cDNA the vector pUC9 was preferred) and given complementary tails (preferably dCTP) in order to obtain complementary single strands at the 3' ends. In the next step the homopolymer-extended double strand cDNA is mixed with the correspondingly complementarily-tailed vector in order to link it under suitable conditions. After recombination has occurred $CaCl_2$-treated E. coli cells are transformed with this mixture and plated out on selective plates. The clones containing HLZ cDNA may be identified by various known methods. In the present invention, screening with radioactively labelled synthetic oligonucleotides is preferred. Using the published amino acid sequence of HLZ protein, two sets of oligonucleotides each 17 bases long were synthesised. Owing to the fact that different codons can specify one and the same amino acid, each set was given a mixture of different oligonucleotides.

The synthesis of all possible combinations ensures that one of the oligonucleotides present forms an optimum pair with the HLZ gene. The use of two individual pools of 17-mer oligonucleotides reduces the possibility that "false" positives will be selected.

In the screening experiments the DNA of those bacterial clones which carry cDNA inserts was transferred to nitrocellulose filters and inserts containing the HLZ gene were identified using the method known as "colony hybridisation". The nitrocellulose filters were hybridised under suitable conditions with the radioactively labelled pools of human lysozyme gene-specific 17-mers. After the identification of corresponding clones, the plasmid DNA of each clone was prepared and the insertion was sequenced using the Maxam and Gilbert method (chemical process) or the Sanger method (synthesis with dideoxynucleotides). Determination of the DNA sequence from the cDNA insertion from positive clones makes it possible to infer the amino acid sequence of the potential protein. Comparison of this sequence with the published HLZ amino acid sequence makes it possible to establish whether the cloned cDNA actually contains the coding region for the HLZ protein.

In general, plasmid vectors containing replicon and control sequences may be used. These sequences should originate from species which are compatible with the host cells. The vector usually carries, in addition to a replication site, recognition sequences which make it possible to select phenotypically in transformed cells. For example, E. coli is usually transformed with pBR322, a plasmid originating from E. coli species (Bolivar, et al., Gene 2, 95 (1977)). pBR322 contains genes for ampicillin and tetracycline resistance and therefore provides a simple means for identifying transformed cells. The pBR322 plasmid or any others must also contain promoters themselves or must be modified so that they can be used by the microorganism to express its own proteins. The promoters most frequently used in the production of recombinant DNA contain the beta-lactamase (penicillinase) and lactose promoter systems (Chang et al., Nature 275, 615 (1978); Itakura et al., Science 198, 1056 (1977); Goeddel et al., Nature 281, 544 (1979) and tryptophan (trp) promoter systems (Goeddel et al., Nucleic Acids Res. 8, 4057 (1980); European application, publication No. 0036 776). Whereas those mentioned above are the commonest promoters, other microbial promoters have also been developed and used. The gene sequence for HLZ may, for example, be used under the control of the leftward promoter of bacteriophage lambda $(P_L)$. This promoter is one of the promoters known to be particularly strong and is also controllable. It can be controlled by means of the lambda repressor, the gene for which has known adjacent restriction cutting sites.

A mutation of this gene, which codes for a thermolabile repressor, can be included in a vector which contains a complete HLZ sequence. If the temperature is increased to 42° C. the repressor is inactivated and the promoter is then maximally active. The total mRNA which is produced under these conditions should be sufficient to obtain a cell which contains, among its new synthetic ribonucleic acids, approximately 10% originating from the $P_L$ promoter. In this way it is possible to establish a clone bank in which a functional HLZ sequence is placed adjacent to a ribosome binding site at varying intervals from the lambda $P_L$ promoter. These clones can then be examined and those with the highest yield selected.

The expression and translation of an HLZ sequence may also be carried out under the control of other regulating systems which may be regarded as "homologous" to the organism in its untransformed form. Thus, for example, chromosomal DNA from a lactose-dependent E. coli strain contains a lactose or lac operon which permits lactose degradation by directing expression of the enzyme beta-galactosidase.

The lac operon control elements may be obtained from the bacteriophage lambda plac 5, which is infectious to *E. coli*. The lac operon of the phage may be obtained from the same bacterial species by transduction. Regulating systems which may be used in the process according to the invention may originate from plasmidic DNA from the same organism. The lac promoter-operator system may be induced by IPTG.

Other promoter-operator systems or parts thereof may be used equally well: for example the arabinose operator, the colicine $E_1$ operator, the galactose operator, the alkaline phosphatase operator, the trp operator, the xylose A operator, the tac-promoter, etc.

Preferably a yeast promoter may be coupled to the HLZ coding region in such a way that effective expression of HLZ is ensured. More particularly, the yeast promoter should be positioned directly in front of the region coding for mature HLZ -with a translation start signal (ATG) inserted at this connecting site. Moreover, this HLZ expression modulus may be inserted in various yeast vectors in order to establish it in yeast, using known methods of yeast transformation. Yeast cells which contain hybrid plasmids may be cultivated in various media and the desired product HLZ may be isolated therefrom and purified by known methods. Alternatively, a yeast signal sequence may be inserted in the construction of the HLZ expression modulus. In this case, yeast cells which have been transformed with a plasmid of this kind are capable of expelling HLZ through their cell walls into the culture medium, from which the desired product—HLZ—can be recovered and further purified.

Yeast cells are particularly preferred as the host organism for expression since yeast cells are easy to cultivate, the conditions for fermentation on a large scale are already established and yeasts are free from endotoxins. Therefore, in the present invention, eukaryotic microorganisms such as yeast cultures may preferably be used. *Saccharomyces cerevisiae* is the most frequently used of the eukaryotic microorganisms, although a number of other species are generally obtainable.

For expression in Saccharomyces, the plasmid YRp7 (Stinchcomb. et al. Nature 282, 39 (1979); Kingsman et al., Gene 7, 141 (1979); Tschumper, et al. Gene 10, 157 (1980)) and the plasmid YEp 13 (Broach et al., Gene 8, 121–133 (1979)(ATCC 37115)) are usually used. The plasmid YRp7 contains the TRPI-gene which provides a selection marker for a yeast mutant which is incapable of growing in tryptophan-free medium; for example ATCC No. 44076. The TRPI-deletion as a characteristic of the yeast host genome constitutes an effective aid to detecting the transformation, in which cultivation is carried out without tryptophan. The situation is similar with the plasmid YEp 13, which contains the yeast gene LEU 2, which can be used to complement a LEU-2 mutant. Suitable promoter sequences for yeast vectors contain the 5'-flanking region of the ADHI gene (Ammerer, G., Method of Enzymology 101, 192–201, 1983), the 3-phosphogylcerate kinase gene (Hitzeman, et al., J. Biol. Chem. 255, 2073, 1980) or another glycolytic enzyme gene (Kawasaki and Fraenkel, BBRC 108, 1107–1112 (1982)), such as the gene for enolase, glyceroaldehyde-3-phosphate dehydrogenase, hexokinase, pyruvate decarboxylase, phosphofructokinase, glucose-6-phosphate isomerase, phosphoglucose isomerase or glucokinase. In the construction of suitable expression plasmids, the termination sequences associated with these genes may also be used in the expression vector at the 3' end of the sequence which is to be expressed, in order to provide polyadenylation and termination of the mRNA.

Other promoters which also have the advantage of transcription controlled by the growth conditions, are the promoter regions of the genes for alcohol dehydrogenase 2, isocytochrome C, acid phosphatase, the degrading enzymes which are connected with nitrogen metabolism, the above-mentioned glyceraldehyde-3-phosphate dehydrogenase and the enzymes which are responsible for metabolising maltose and galactose. Promoters which are regulated by the yeast mating type locus, for example promoters of the genes BAR1, MEC1, MEC2, STE2, STE5 may be inserted in temperature-regulated systems by using temperature dependent sir mutations. (Rhine, Ph.D. Thesis, University of Oregon, Eugene, Oreg. (1979), Herskowitz and Oshima, The Molecular Biology of the Yeast Saccharomyces, part I, 181–209 (1981), Cold Spring Harbor Laboratory). These mutations influence the expression of the resting mating type cassettes of yeasts and, indirectly, the mating type-dependent promoters. In general, however, any plasmid vector which contains a yeast-compatible promoter, original replication and termination sequences, is suitable.

The presence of the intact HLZ cDNA sequence makes it possible to construct the HLZ gene for expression in other microorganisms, such as yeast.

Therefore, for the expression of HLZ in yeast cells according to the invention, it is possible to use secretion plasmids which are made up either of the elements ADHI promoter -α-factor leader -HLZ gene-ADHII terminator or of the elements α-factor promoter-α-factor leader-HLZ gene -α-factor terminator. The DNA sequences of the ADHI promoter, ADHII terminator and α-factor gene are known. (Jeffery, L., et al., J. Biol. Chem. 257, 3018–25, 1982; Russell, D. W. et al., J. Biol. Chem. 258, 2674–82, 1983; Nucleic Acids Res. 12, 4049–63, 1983).

An HLZ gene prepared in this way may be functionally connected to a selected yeast promoter. An expression unit of this kind may also be integrated in various yeast vectors. These are capable of transforming yeast, which leads to the synthesis of human lysozyme.

For expression of HLZ under preferential control of the ADHI promoter, it is possible to construct a plasmid which contains the complete α-factor leader behind the 3' end of the ADHI promoter. The DNA sequence coding for mature HLZ (HLZ gene) is ligated to the 3' end of the α-factor leader in the correct orientation towards the α-factor leader. A construction which results in an exact N-terminus upon expression of the HLZ gene is preferred. For the final construction with regard to the expression cassette, the ADHII terminator sequence which effects uniform termination of the HLZ gene and contributes to the stability of the mRNA is incorporated in such a way that it is located immediately adjacent to the stop codon of the HLZ gene. An expression plasmid of this kind contains all the elements described in the correct sequence and orientation relative to one another, and the exact transitions between the elements ADHI promoter, α-factor leader, HLZ gene and ADHII terminator. It is particularly advantageous if the connection between the α-factor leader and the subsequent HLZ gene is made so that the protease cutting site responsible for maturation of the α-factor is located after LYS ARG precisely in front of the sequence for the first amino acid of the mature HLZ, so that an exact N-terminus of the HLZ protein formed by the host cell is obtained.

An expression cassette of this kind may be ligated in various yeast expression plasmids. The multicopy plasmids YEp13 (Broach, J. R. et al. Gene 8, 121–133, 1979), PJDB207 (DSM 3181, deposited 28.12.1984), YIp5 (Struhl, K. et al., Proc. Natl. Acad. Sci. USA 76, 1035–1039, 1979) and pEAS102 are preferred for this. The vector pEAS102 may be obtained by partially digesting YIp5 with PstI and totally digesting YIp5 with BamHI and ligating the isolated 4.3 kb fragment (which contains the URA3 gene) with the 4.4 kb BamHI/PstI fragment of pJDB207. With these yeast vectors carrying an expression cassette of this kind, yeast cells of both mating types may be transformed by known methods. The HLZ produced by such transformants and released into the culture medium can easily be isolated by known methods of protein purification.

It is equally preferable for expression of the HLZ gene to be carried out under the control of the α-factor promoter. To do this, the DNA sequence coding for mature HLZ is ligated in the correct orientation between the α-factor promoter and the α-factor leader. In order to construct a complete expression cassette, the α-factor promoter with the α-factor leader, HLZ gene and α-factor terminator are arranged one behind the other. In this case also, the same transition is established between the 3' end of the α-factor leader and the 5' end of the HLZ gene, as described in the production of the expression cassette under the control of the ADHI promoter. An expression cassette of this kind can be incorporated in the yeast expression plasmids described above, which can then be used to transform yeast cells by known methods.

Preferred hosts in this case are yeast strains of the mating type α. The cultivation of such transformants and the isolation of the HLZ released by them are carried out by known methods.

These constructions give rise to a number of advantages:
1. Uniform termination of the mRNA and hence greater stability of the mRNA.
2. Ease of isolation of HLZ from the supernatant of the culture medium.
3. A high proportion of HLZ having the correct tertiary structure since disulphide bridges can be formed more easily in the secreted protein than inside the yeast cell.
4. During secretion the signal or leader peptide component is precisely separated from the mature HLZ endoproteolytically.

In this way an accurately defined N-terminus of the protein is obtained. The mature HLZ protein has a lysine at the N-terminus. The plasmid construction can be selected so that the protease cutting site is positioned in front of the lysine codon in the secretion plasmid. Accordingly, the first amino acid of the secreted HLZ is lysine. In intracellular production, a start ATG (methionine) has to be placed in front of the first amino acid of the mature lysozyme to enable translation to begin at all. Unless this methionine is removed by a cellular mechanism it may be very disruptive (activity, stability, antigenicity).

In addition to microorganisms, cultures of multicellular organisms are also suitable hosts for the expression of HLZ. Theoretically, any of these cultures may be used, whether from vertebrates or invertebrate animal cell cultures. However, the greatest interest has been shown in vertebrate cells, with the result that the replication of vertebrate cells in culture (tissue culture) has become a routine procedure in recent years. (Tissue culture, Academic Press, Kurse and Patterson, Editors (1973)). Examples of useful host cell lines of this kind include VERO- and HeLa-cells, Chinese hamster ovary (CHO)-cells and W138, BHK, COS-7 and MDCK- cell lines. Expression vectors for these cells usually contain a replication site (if necessary), a promoter which is located in front of the gene which is to be expressed, together with any necessary ribosome binding site, RNA splicing site, polyadenylation site and transcription terminating sequences.

For use in mammalian cells, the control functions on the expression vectors are frequently taken from viral material. For example, the promoters normally used come from Polyoma, Adenovirus 2, and, most frequently, from *Simian virus* 40 (SV 40). The start and end promoters of SV 40 are particularly useful, since both are easily obtainable as a fragment from the virus and also contain the vital replication site of SV 40 (Fiefs et al., Nature 273, 113 (1978)). It is also possible to use smaller or larger fragments of SV 40, provided that they contain the approximately 250 bp long sequence which extends from the Hind III cutting site to the BglI cutting site in the vital replication site. Moreover it is also possible and often desirable to use promoter or control sequences which are normally linked to the desired genetic sequences, provided that these control sequences are compatible with the host cell systems.

A replication site may either be provided by corresponding vector construction in order to incorporate an exogenic site, for example from SV 40 or other viral sources (e.g. Polyoma, Adeno, VSV, PBV, etc.) or it may be provided by the chromosomal replication mechanisms of the host cell. If the vector is integrated in the host cell chromosome, the latter measure is usually sufficient.

Transformation of the cells with the vehicles can be achieved by a number of methods. For example, it may be effected using calcium, in which case either the cells are washed in magnesium and the DNA is added to the cells suspended in calcium or the cells are exposed to a coprecipitate of DNA and calcium phosphate. In the subsequent gene expression, the cells are transferred to media which select for transformed cells. The polypeptide according to the invention is not exclusively the mature human lysozyme (HLZ) which is described in detail but may also be any biologically active variation or modification of this polypeptide. A biologically active variation or modification of HLZ is a ploypeptide that has changes in the amino acid sequence from the naturally occurring HLZ but maintains essentially the same biological activity as the naturally occurring HLZ. These modifications include, for example, shortening of the molecule at the N or C- terminal end and replacement of amino acids by other groups, whereby the activity is not substantially affected.

The invention relates not only to gene sequences which code specifically for the HLZ mentioned, but also to modifications which are readily and routinely obtained by mutation, degradation, transposition or addition. Any sequence which codes for the HLZ described above (i.e. which has the corresponding known biological spectrum of activity) and is degenerate compared with those shown is also included; any one skilled in the art is capable of determining degenerate DNA sequences of coding regions. Similarly, any sequence which codes for a polypeptide having the activity spectrum of HLZ and which hybridises with the sequences shown (or parts thereof) under stringent conditions (for example, conditions which select for more than 85% and preferably more than 90% homology) are also included.

The substance according to the invention may be formulated in known manner in order to produce pharmaceutically usable compositions, the polypeptide according to the invention being used either on its own or administered in conjunction with other components such as various antibiotics (tetracycline, bacitracin), enzymes (alpha-amylase, papain) or vitamins.

The following examples, which are not intended to restrict the invention, describe it in detail.

SHORT DESCRIPTION OF THE DRAWINGS

FIG. 2 shows the result of dot-blot hybridisation.

FIG. 4a shows the DNA sequence of the HLZ cDNA clone HL 14-1

FIG. 5 shows a comparison between the published HLZ amino acid sequence (top row) and the amino acid sequence derived from the cDNA of the clone HL 14-1 (bottom row)

Figure 8:
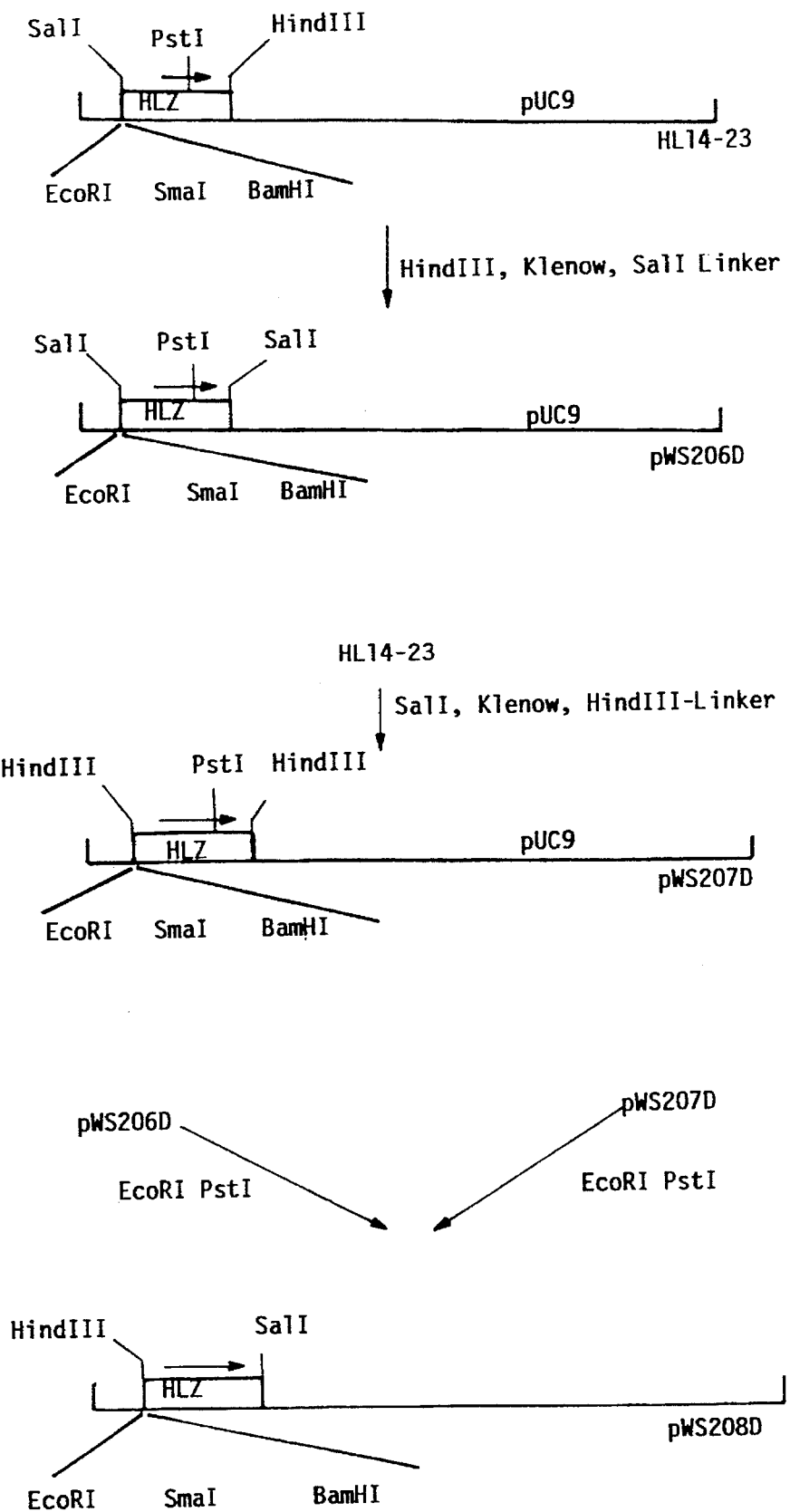
Figure 9:
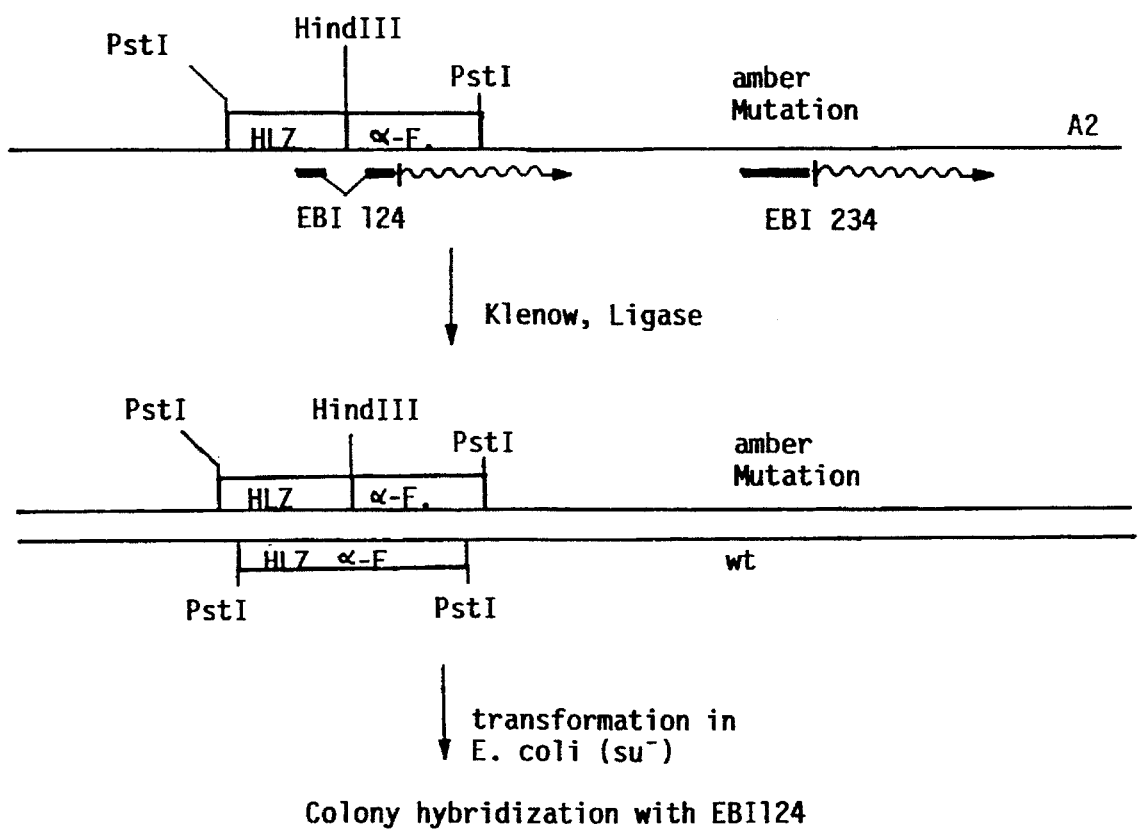
Figure 10:
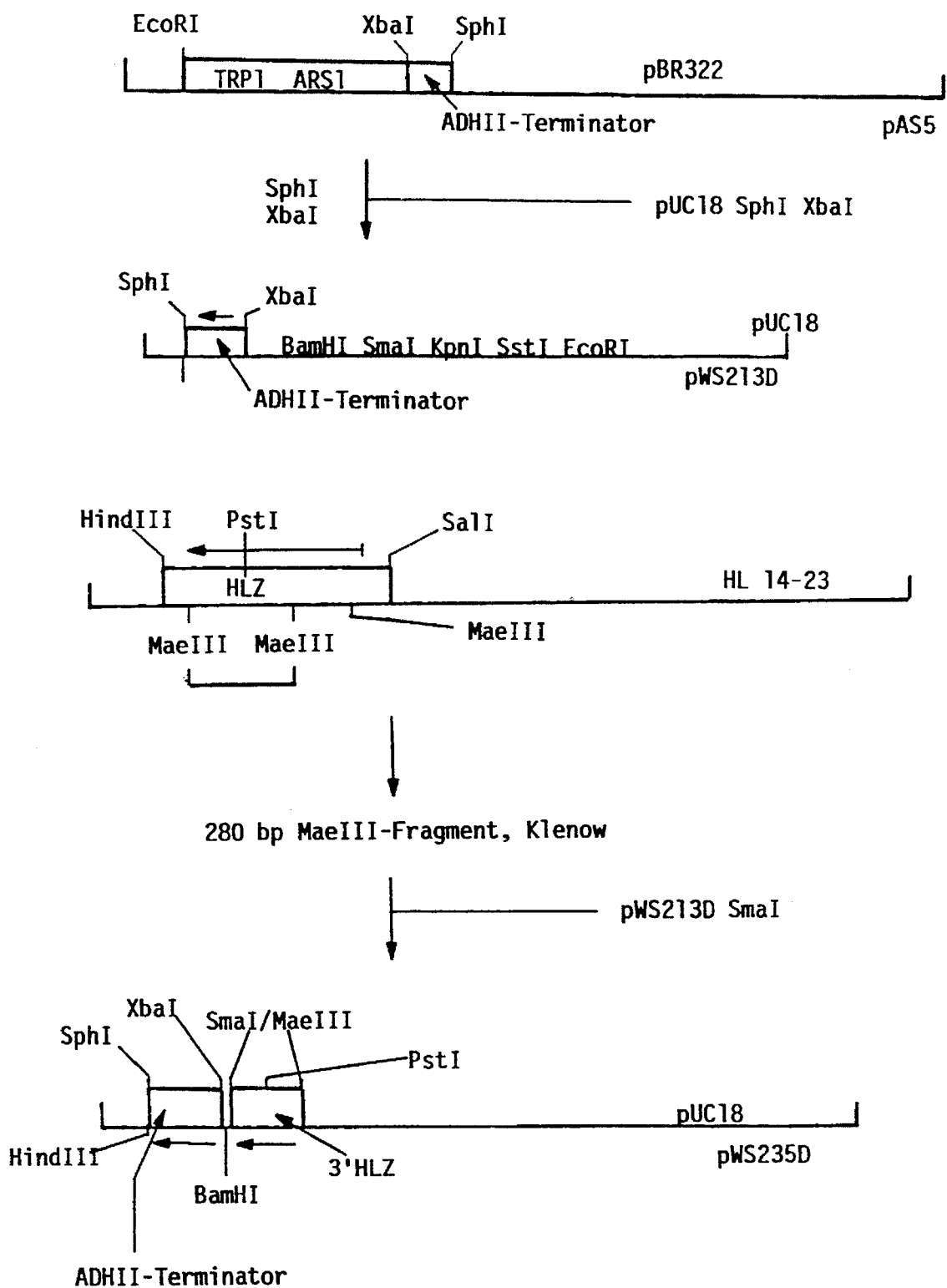
Figure 11:
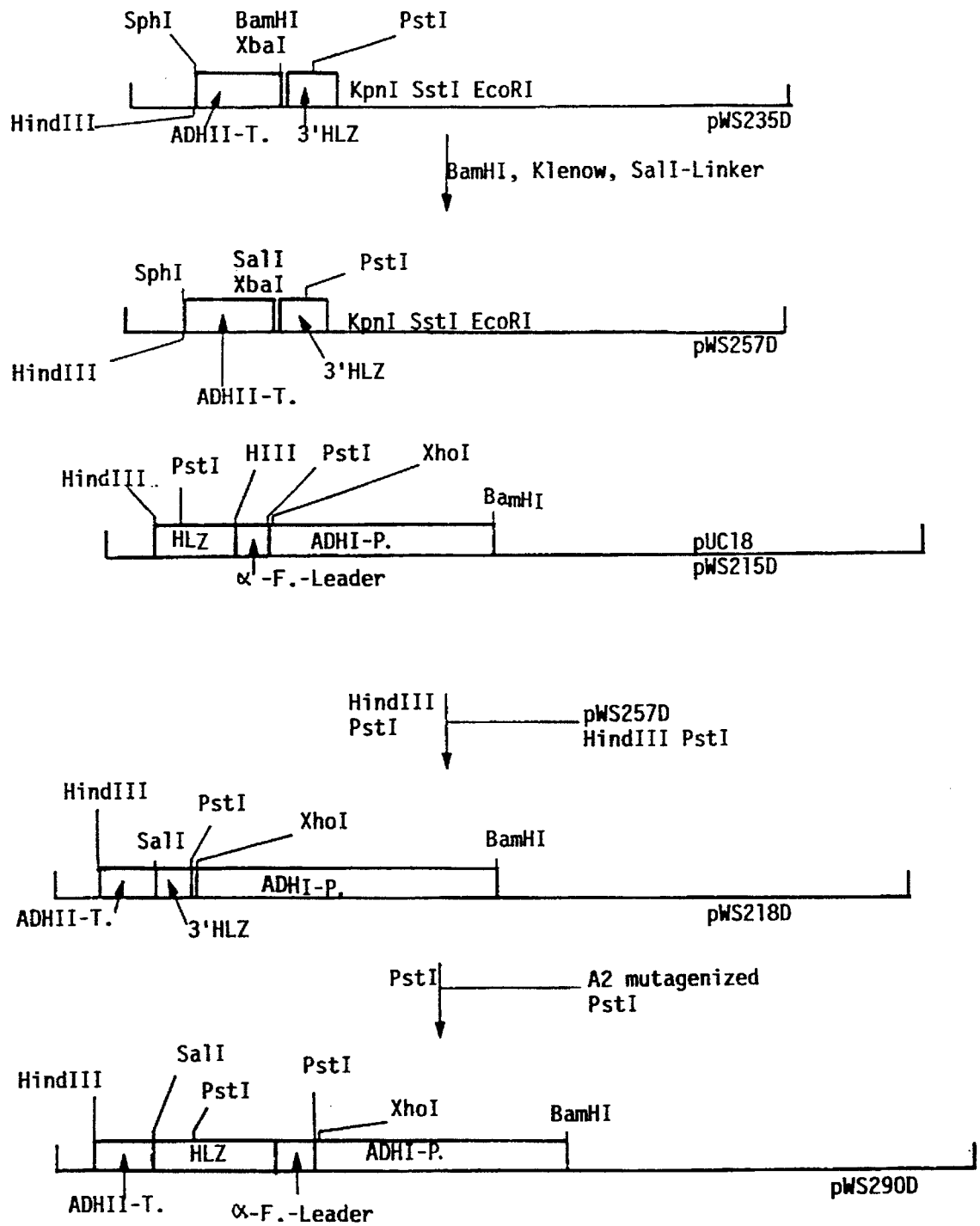

FIG. 7 shows the linking of the ADHI promoter to the α-factor leader and the further construction to form pWS215D, in which the HLZ gene is connected to the α-factor leader in the correct orientation FIG. 8 shows both the linker ligation with HindIII linkers (Example 8b) and also those with SAII and HindIII linkers (Example 9b, leading to pWS208D), for the purpose of incorporating the HLZ gene in the correct orientation with respect to the α-factor leader or to the α-factor promoter or terminator FIG. 9 shows the in vitro mutagenesis with the synthetic oligonucleotides EBI 124 and EBI 234, with the purpose of establishing an exact transition between the α-factor leader and the HLZ gene FIG. 10 shows the construction of pWS235D in which the exact 3' end of the HLZ gene has been incorporated in the correct orientation in front of the ADHII terminator FIG. 11 shows, at the top, the distance of the BamHI site (pWS257D) between the HLZ gene and the ADHII terminator and the final construction to form the expression cassette (pWS290D)

Figure 12:
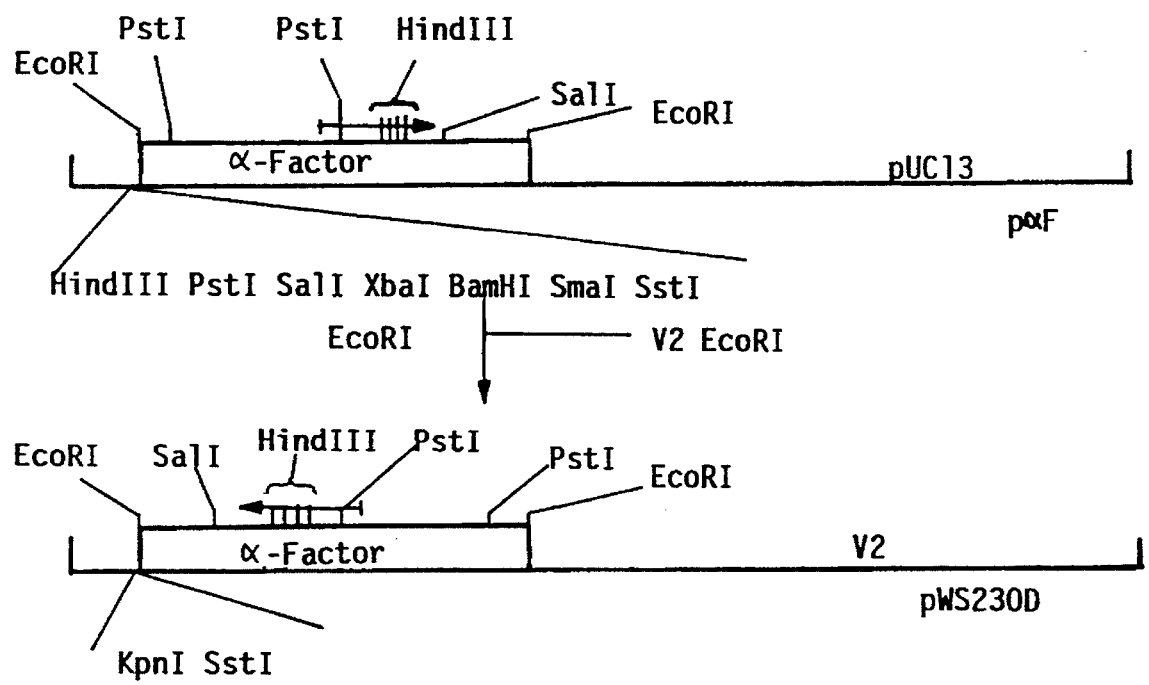

FIG. 12 shows how the α-factor gene was cloned from the puC13 derivative pαF as an EcoRI-fragment in the vector V2 (puC18 derivative, for its construction see Example 9a) (pWS230D)

Figure 13:
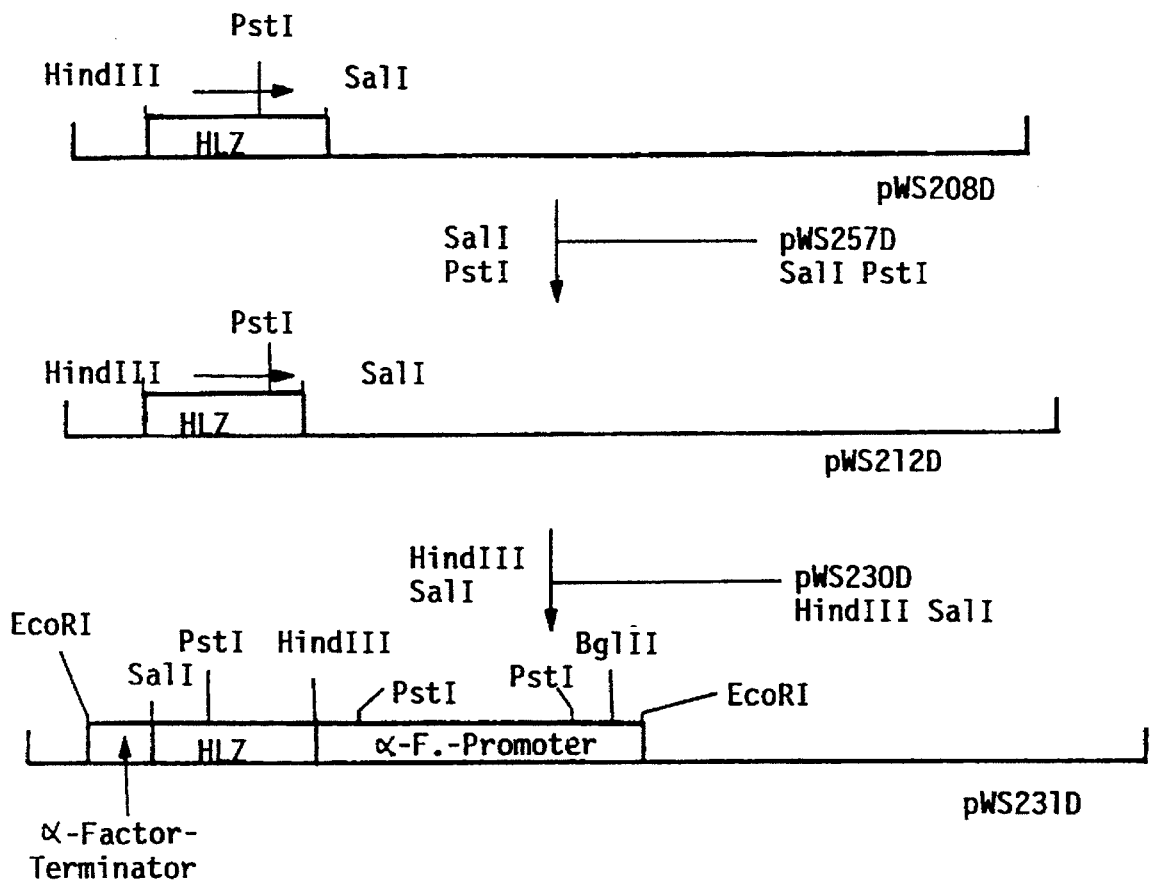

FIG. 13 illustrates the way in which the HLZ gene is connected to the α-factor promoter and terminator in the correct orientation (pWS231D)

Figure 14B:
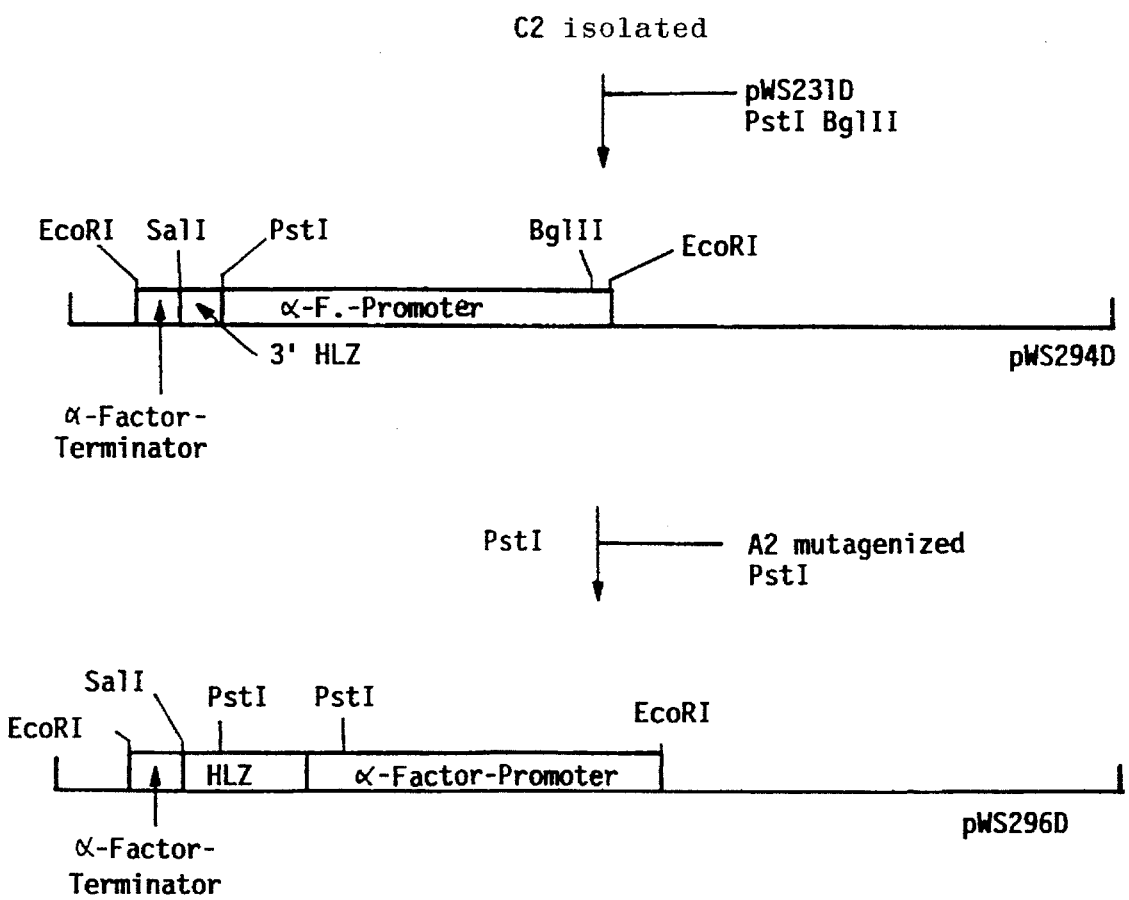

FIGS. 14a and 14b show the distance of the PstI site closest to the 5' end of the α-factor gene (pWS294D) and the final position of the expression cassette pWS296D under the control of the α-factor promoter by ligation of the mutagenised PstI fragment A2, shown in FIG. 9, in the single PstI site of pWS294D.

DESCRIPTION OF THE PREFERRED EMBODIMENTS

Abbreviations used in the Examples

| | |
|---|---|
| HLZ | Human-Lysozyme |
| RPMI | Roswell Park Memorial Institute |
| TrisHCL | Tris-(hydroxymethyl)-aminomethane, pH adjusted with HCl |
| EDTA | Ethylenediaminetetra acetic acid |
| DEP | Diethylpyrocarbonate |
| SDS | Sodium dodecyl sulphate |
| NaAc | Sodium acetate |
| BSA | Bovine serum albumin |
| DTT | 1,4-dithiothreitol (1,4-dimercapto-2,3-butandiol) |
| PCI | Phenol:Chloroform:Isoamylalcohol (15:24:1) |
| Beta-NAD | Beta-nicotinamide adenine dinucleotide |
| sscDNA | Single strand cDNA |
| E. coli | Escherichia coli |
| SSC | Solution of 0.15M NaCl, 0.015M sodium citrate adjusted to pH 7 with 10N NaOH. |
| Denhardt's Solution | Solution of 0.1% Ficoll, 0.1% polyvinyl-pyrrolidone, 0.1% BSA. |
| TBE | Solution of 0.082M Tris, 0.082M boric acid, 0.002M EDTA pH 8. |

EXAMPLE 1

Assay of HLZ activity in cell line U-937

It has been reported that the human haematopoietic cell line U-937 produces human lysozyme (16). In order to use the U-937 cell line as a source of polyA$^+$RNA for synthesis of HLZ cDNA, we have assayed the activity of HLZ released to the medium by U-937 cells. Freshly inoculated U-937 cell line culture in RPMI 1640 medium containing 10% fetal calf serum, penicillin (100 units/ml) and streptomycin (50 units/ml) was grown at 37° for 3 days to the density 3×10$^5$ cells/ml. Cells were then removed by centrifugation and activity of HLZ released to the medium was assayed by the method described by Gold and Schweiger (17). After 2 hours incubation with radioactive substrate the amount of released radioactivity was measured in 100 μl aliquots taken out of 2 ml incubation mixtures. RPMI medium alone was used as a negative control. Quantities of HLZ secreted by the U-937 cells were calculated from a prepared standard curve (activity of human lysozyme from human milk [Sigma] in RPMI medium).

The results are presented in Table I.

TABLE I

| Medium dilutions | CPM released per 100 μl of incubation mixture | CPM released per 100 μl of medium | Amount of secreted HLZ (μg/ml) |
|---|---|---|---|
| 2× | 10 457 | 20 914 | 2.09 |
| 4× | 3 963 | 15 852 | 1.59 |
| 10× | 1 485 | 14 850 | 1.49 |
| 20× | 794 | 15 880 | 1.59 |

As presented in Table I, U-937 cells release to the RPMI medium about 1.5 μg HLZ per 1 ml of medium. It was concluded that the U-937 cell line could be a useful source of HLZ mRNA.

EXAMPLE 2

Preparation of RNA containing human lysozyme mRNA a) Isolation of total RNA

The human histiocytic lymphoma cell line U-937 was grown in RPMI medium 1640 containing 10% fetal calf serum, penicillin (100 units/ml) and streptomycin (50 units/ml) at 37° C. (16). Cells from 1.6 liters of culture were collected by centrifugation, washed once with 50 ml of ice-cold 10 mM Tris HCl pH 7.4/140 mM NaCl/1.5 mM MgCl$_2$, and suspended in 10 ml of ice-cold 10 mM Tris HCl pH 8.4/140 mM NaCl/1.5 mM MgCl$_2$. The non-ionic detergent, Nonidet P40, was added to give a final concentration of 0.5%. The suspension was kept on ice for 5 minutes and then mixed vigorously for 10 seconds to lyse the cell membranes. The nuclei were then removed by centrifugation at 4° C. To 10 ml of supernatant, the following solutions were added: 0.5 ml of 20% SDS, 0.25 ml of 2M Tris HCl pH 9.0, 0.1 ml of 500 mM EDTA pH 7.5. An equal volume of freshly distilled phenol, equilibrated with 10 mM Tris HCl pH 8/1 mM EDTA, was added and the sample was shaken vigorously for 10 minutes, followed by centrifugation to separate the phases. The aqueous phase was extracted twice as described above, and finally with an equal volume of chloroform. 3M potassium acetate (1/10 volume of aqueous phase) was added followed by 2.5 volumes of ethanol. The solution was kept at −20° C. overnight, the RNA precipitate was collected by centrifugation, washed once with 3 ml of 70% ethanol and dried in a vacuum. The RNA was dissolved in 3 ml of water and precipitated, collected, dried and redissolved as above. About 8 mg of RNA were obtained.

b) Isolation of polyA⁺RNA

PolyA⁺RNA was isolated from the total RNA on oligo(dT)-cellulose (P-L Biochemicals, Inc.). 0.5g oligo(dT)-cellulose was suspended in sterile water and left overnight at 14° C. Next day a column (Biorad plastic, 18 cm, 0 1.5 cm) washed with DEP-treated sterile H₂O was loaded with 0.5 g oligo(dT)-cellulose, then washed with 3 ml proteinase K (Type XI, Sigma) solution and left for 15 min at ambient temperature. Proteinase K was dissolved in 0.1× loading buffer (1× loading buffer: 50 mM Tris.HCl pH 7.4, 1M NaCl, 1 mM EDTA, 0.2% SDS) to a final concentration of 1 mg/ml. The column was then subsequently washed with 5 ml sterile 0.1M NaOH, then with sterile H₂O until the pH of the eluant was 8, and finally with 10 ml 1× loading buffer. Total RNA resuspended in 500 μl sterile H₂O was diluted with 4.5 ml loading buffer, heated for 5 min at 65° (water bath) and loaded on the prepared oligo(dT)-cellulose column. The eluant was collected, reheated at 65° for 5 min and re-loaded on to the column. The column was washed with 7 ml loading buffer in order to wash out polyA RNA. 1 ml fractions were collected and the OD₂₆₀ of each fraction was measured. PolyA⁺RNA was eluted with 5 ml of sterile water. Both polyA RNA and polyA⁺RNA were precipitated out of 0.3M NaAc with ethanol overnight at −20°.

EXAMPLE 2

Assay for the presence of HLZ mRNA a) Synthesis of oligonucleotides of mixed sequence Two pools of oligonucleotides of mixed sequence homologous to HLZ were synthesised by the solid-phase phosphotriester method (20). The sequence of amino acid residues 63-68 (Tyr Trp Cys Asn Asp Gly) from the NH₂-terminus of human lysozyme protein (21,22,23) was chosen for the construction of a 17-met oligonucleotide mixed probe Ei-ON19. Ei-On19 probe consists of sixteen mixed oligonucleotides as shown:

The sequence of amino acid residues 26–31 (Ala Asn Trp Met Cys Leu) from the NH₂-terminus of human lysozyme protein (21,22,23) was chosen for the construction of a 17-mer oligonucleotide mixed probe Ei-ON20. The Ei-ON20 probe consists of thirty-two mixed oligonucleotides as shown:

b) Primer extension analysis

The mRNA isolated from the U-937 cell line was analysed for the presence of HLZ mRNA by the primer extension method. 100 ng of Ei-ON19 or Ei-ON20 were labelled at the 5' end in the reaction mixture of 20 μl containing 70 mM Tris HCl, pH 7.6, 1 mM MgCl₂, 30 μCi of (gamma-$^{32}p$) ATP (5000 Ci/mmol, Amersham PB.218), 100 μg/ml BSA, 10 mM DTT, 1 mM spermidine and 2-4 units of polynucleotide kinase (New England BioLabs) for 60 min at 37° C. The reaction was stopped by heating the mixture for 10 min at 70° C.

The primer extension reaction is carried out in a reaction volume of 40 μl containing 50 mM Tris HCl, pH 8.3, 10 mM MgCl₂, 10 mM DTT, 4 mM sodium pyrophosphate, 1.25 mM dGTP, 1.25 mM dATP, 1.25 mM dCTP, 1.25 mM dTTP, 150 ng of mRNA isolated from the U-937 cell line, 40 ng of radioactively labelled Ei-ON19 or Ei-ON20 and 200 units of reverse transcriptase (BRL) for 60 min at 42° C. The reaction is stopped by addition of 50 μl of 50 mM EDTA and subsequently extracted with PCI and precipitated with ethanol. Products of primer extension are pelleted by centrifugation, dried and dissolved in 20 μl of a dyed formamide solution consisting of 90% of deionised formamide, 10% of 10×TBE, 0.1% xylene cyanol FF and 0.1% bromphenol blue.

Figure 1:
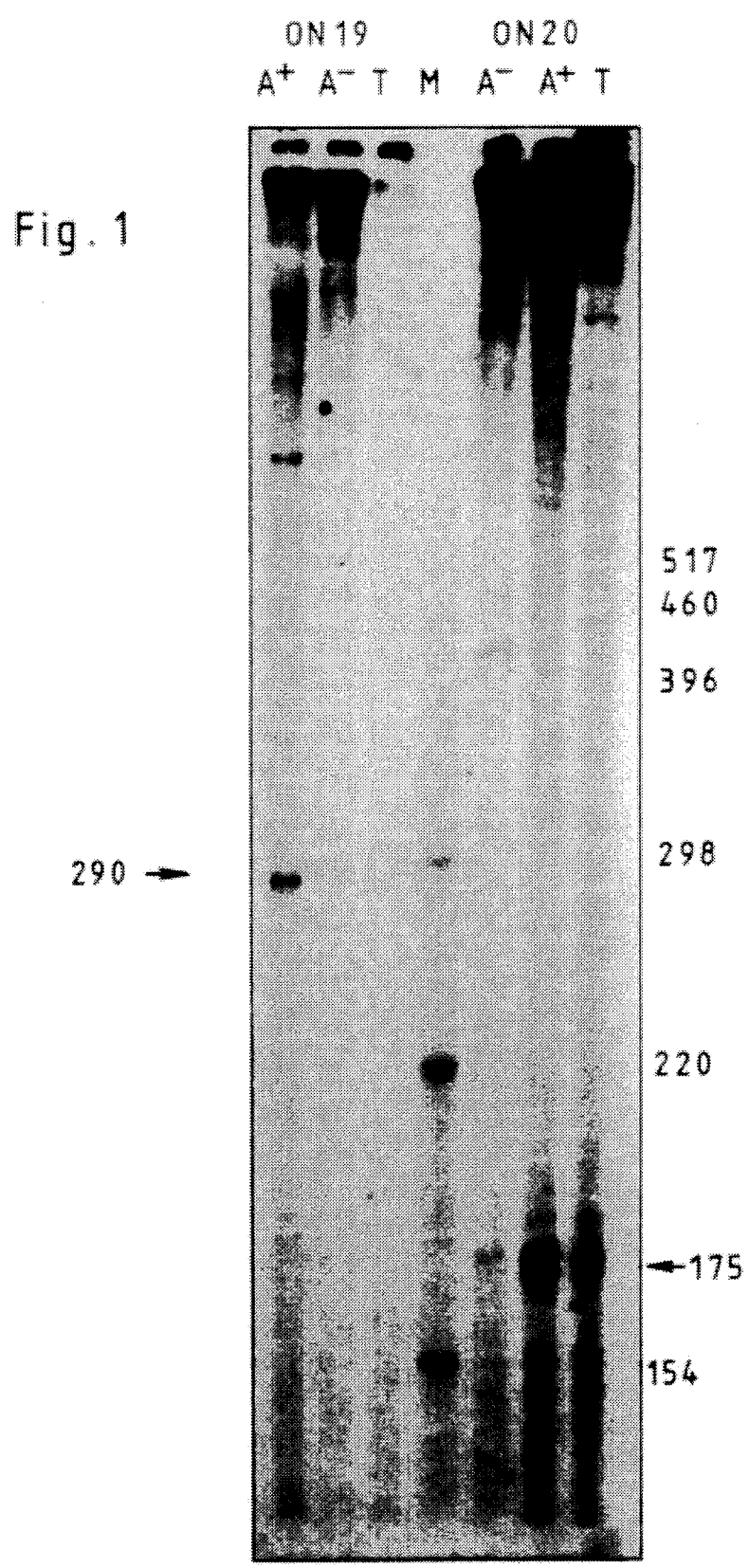
FIG. 1 shows the results of the primer extension experiment in which Ei-ON19 and Ei-ON20 were the primers and the template was the RNA isolated from the cell line U-937

10 μl from each sample is loaded on 5% acrylamide/8M urea gel and electrophoresis is run for 2 h at 15 watts. The gel is dried and exposed in a Kodak X-Omatic cassette C-2 to Kodak X-Omat RP X-ray film. The results of this experiment are shown in FIG. 1.

Since both primers, Ei-ON19 and Ei-ON20, are complementary to HLZ mRNA one might have expected to detect specific products of extension of these primers on the HLZ mRNA template with reverse transcriptase (24). Since the length of HLZ mRNA was not known, the length of synthesised DNA could not be predicted. However, the following was established: the primer Ei-ON19 binds to the HLZ mRNA in the region which codes for amino acid residues 63–68, that is to say the length of synthesised DNA must be at least 203 bp+X (where X is the number of nucleotides which belong to the leader sequence and the 5' noncoding region). The same calculation for the primer Ei-ON20 gives the value 92 bp+X. There should therefore be two bands differing in length by 111 bp. From the results presented in FIG. 1, it can be seen that the strongest band synthesised with the primer Ei-ON19 is about 290 bp long and the strongest band obtained with primer Ei-ON20 is about 175 bp. The difference between them (115 bp) is very close to the predicted value and it was concluded that the analysed preparation of mRNA isolated from the U-937 cell line contains HLZ mRNA.

EXAMPLE 4

Construction of the U-937 cDNA library a) Synthesis of cDNA

Synthesis of the first strand cDNA is carried out in a reaction volume of 50 μl containing 50 mM Tris HCl pH 8.3, 10 mM MgCl₂, 10 mM DTT, 4 mM sodium pyrophosphate, 1.25 mM dGTP, 1.25 mM dATP, 1.25 mM dTTP, 0.5 mM dCTP, 20 μCi of (α-32P) dCTP (3000 Ci/mmol, Amersham, PB. 10205), 100 μg/ml of oligo d(T)₁₈ (New England BioLabs), 40–100 μg/ml of polyA⁺RNA isolated from the U-937 cell line and 250 units of reverse transcriptase (BRL). The reaction proceeds for 60 min at 42° C. The reaction is stopped by adding 50 µl of 50 mM EDTA and the products of the reaction are extracted with PCI. The RNA:DNA hybrid is precipitated with ethanol out of 2M NH₄acetate at −20° C. overnight. The amount of first strand synthesised is estimated by assaying TCA insoluble radioactivity. From a single reaction, between 200 and 300 ng of single stranded cDNA are usually obtained. For second strand synthesis the single stranded cDNA was pelleted by centrifugation, washed once with 80% ethanol, dried and dissolved in a suitable volume of distilled $H_2O$. To convert sscDNA into double stranded cDNA (dscDNA) up to 500 ng of sscDNA can be processed in a reaction volume of 100 µl containing 20 mM TrisHCl, pH 7.5, 5 mM $MgCl_2$, 10 mM $(NH_4)_2SO_4$, 100 mM KCl, 0.15 mM β-NAD, 50 µg/ml BSA, 40 µM dNTPs, 8 units/ml of E. coli RNase H (BRL), 230 units/ml E. coli DNA polymerase I (New England BioLabs), 10 units/ml E. coli DNA Ligase (New England BioLabs). The reaction mixture is sequentially incubated for 60 min at 12° C. and for 60 min at 22° C. The reaction is stopped by addition of EDTA to give a final concentration of 20 mM. The dscDNA is extracted with PCI and precipitated as above (15).

b) Cloning of dscDNA

A cloning vector with low transformation background is prepared as follows: 300 µg of pUC9 plasmid DNA are cut to completion with PstI restriction endonuclease. The digested plasmid DNA is purified through agarose gel electrophoresis, electroeluted and precipitated with ethanol. Agarose-gel purified vector yields in transformation experiments about 1–2 colonies/ng, whereas transformation efficiency with supercoiled pUC9 was about 2000–4000 colonies per ng of plasmid DNA.

pUC9 plasmid DNA thus prepared was subsequently tailed in a reaction volume of 50 µl containing 100 mm potassium cacodylate pH7.5, 2 mM $COCl_2$, 0.2 mM DTT, 0.9 mM dCTP, 5 µCi of (5-³H) dCTP (19 Ci/mmol, Amersham TRK.352), 5 mg/ml BSA, 28 ug of PstI cut pUC9 plasmid DNA and 45 units of terminal transferase (PL-Biochemicals). The reaction mixture was incubated for 5 min at 22° C. the reaction was stopped by the addition of 50 µl of 25 mM EDTA and subsequent incubation for 15 min at 70° C. Under these conditions 22 nucleotides are added to each 3' end, a length that is required for maximum transformation efficiency (19). Tailing of the dscDNA with dGPT was carried out under similar conditions, except that about 100 ng of dscDNA was used per reaction with 30 units of terminal transferase for 30 min at 37° C. The reaction was stopped by addition of 50 µl 25 mM EDTA and heat-inactivated for 15 min at 70° C. The analytical annealing of dGTP-tailed dscDNA with dCTP-tailed pUC9 vector DNA was done in 50 µl containing 10 mM Tris HCl pH 7.5, 1 mM EDTA, 150 mM NaCl for 120 min at 58° C. Different ratios of dscDNA to vector DNA were used to find the maximum number of clones obtainable per weight input of dscDNA. Transformation of $CaCl_2$-competent E. coli RRI cells (19) was carried out by mixing 100 µl of these cells with 50 ul of annealing reaction mixture and subsequent plating onto LB Plates containing 50 µg/ml ampicillin. The ratio which gave the highest number of transformants was used in scale-up experiments to establish the final cDNA library. Using an amount of 50 ng of dscDNA about 20,000 independent clones were generated.

EXAMPLE 5

Screening of the U-937 cDNA library for HLZ clones a) Colony hybridisation

The cDNA library was screened for positive transformants containing a fragment or a whole HLZ gene. The cDNA library was screened first by colony hybridisation. The transformants which seemed to be positive were further screened by dot blot analysis.

Transformants were grown overnight on LB+ampicillin (50 µg/ml) plates at 37° C. Colonies were then transferred to nitrocellulose filters (0.45 µm, Schleicher and Schuell). Both plates and filters were marked in such a way that identification of positive transformants would be possible. Filters carefully placed on plates were left at room temperature (RT) for 20 min, then lifted up and placed (colonies uppermost) on a 3MM filter (3MM Chr, Whatman) saturated with 0.5N NaOH/1.5M NaCl. After 15 min incubation the filters were transferred to a dry 3MM filter to remove excess NaOH and left for 3 min on a 3MM filter prewetted with 1M Tris HCl pH7/1.5M NaCl. Filters were then dumped for 20 sec into 3× SSC, air dried and baked at 80° C. for 2 hours. Filters thus prepared were prewashed overnight at 65° C. with slow agitation in a buffer containing 3× SSC, 0.1% SDS (Serva), 10 mM EDTA. The buffer was changed several times. Prewashing was considered complete when no visible traces of bacterial colonies could be detected on the filters. Just after washing, the filters were prehybridised in a solution containing 6× SSC, 1× Denhardt's solution, 0.5% SDS, 100 µg/ml denatured calf thymus DNA (Sigma), 0.05% sodium pyrophosphate. After 3 hours incubation at 37° C., the filters were hybridised overnight at 37° C. with (gamma-³²P)ATP labelled 17-mer Ei-ON19 in a solution containing 6× SSC, 1× Denhardt's solution, 20 µg/ml yeast tRNA (Type XX, Sigma), 0.05% sodium pyrophosphate, kinased 17-met Ei-0N19. The kinase reaction is described in Example 3. After hybridisation, the filters were washed in 6× SSC, 0.5% sodium pyrophosphate as follows: 3 times for 5 min at RT, 30 min at 37° C., 10 min at 47° C. and 10 min at 53° C. (optional). The filters were then air dried and exposed on X-ray film (X-Omat RP, Kodak) with a Dupont intensifying screen for 24 h at −70° C. After the films were developed, 48 colonies which gave an undoubtedly stronger signal than background were chosen for further analysis (dot-blot analysis).

b) Dot-blot hybridisation 2 ml samples of LB containing 30 µg/ml ampicillin were inoculated with the 48 chosen colonies. Cultures were grown overnight at 37° C. with vigorous agitation. DNA preparations were obtained by the method of Birnboim and Doly (25). Each DNA preparation was suspended in 67.5 µl $H_2O$. Addition of 7.5 µl 4N NaOH was followed by 1 hour incubation at 65° C. in a water bath. The samples were then cooled on ice and 20 µl 1.5N HCl and 195 µl 2× SSC were added, respectively. The total volume of each sample was 290 µl. 145 µl portions were filtered through a Bio-Dot apparatus (Bio-Rad) in order to fix DNA to two nitrocellulose filters. Before filtration the nitrocellulose filters were presoaked for 20 min in 2× SSC. After filtration the filters were air dried and baked at 80° C. for 2 hours. One filter was hybridised with (gamma-³²P) ATP labelled Ei-ON19 17-mer, another filter with (gamma-³²P) ATP labelled Ei-ON20 17-mer. The conditions for hybridisation and washing are described in Example 5a. The filters were exposed for 6 hours at −70° C. on Kodak X-Omat RP X-ray film. Six clones which produced positive hybridisation signals were identified and original transformants were named: pHL2, pHL8, pHL14-1, pHL21, pHL23 and pHL35. The sizes of the cDNA inserts in the chosen clones were estimated by restriction analysis. DNA of the said clones obtained by the method of Birnboim and Doly was digested with BamHI and HindIII and run on a 0.8% agarose minigel for 4 hours (150 V). Plasmids pHL14-1, pHL21 and pHL23 possess inserts 500 bp long. The inserts of pHL2 and pHL8 are 300 bp long.

EXAMPLE 6

Structure and DNA sequence of HLZ cDNA (clone HL 14-1)

Figure 3A:
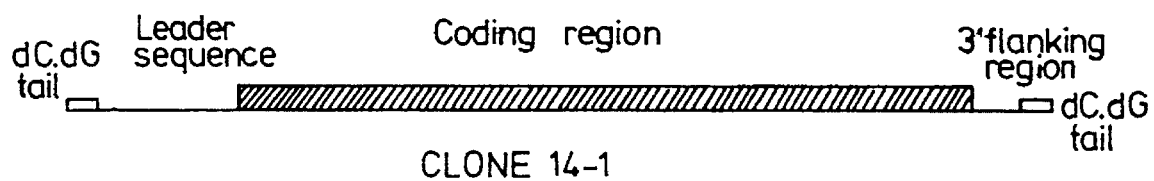
FIG. 3a shows the structure of HLZ cDNA (clone HL 14-1)

One of the positive clones (Example 5b) designated HL14-1 contains a cDNA insert about 500 bp long and was chosen for more detailed analysis. The structure of HLZ cDNA is shown in FIG. 3a.

Figure 3B:
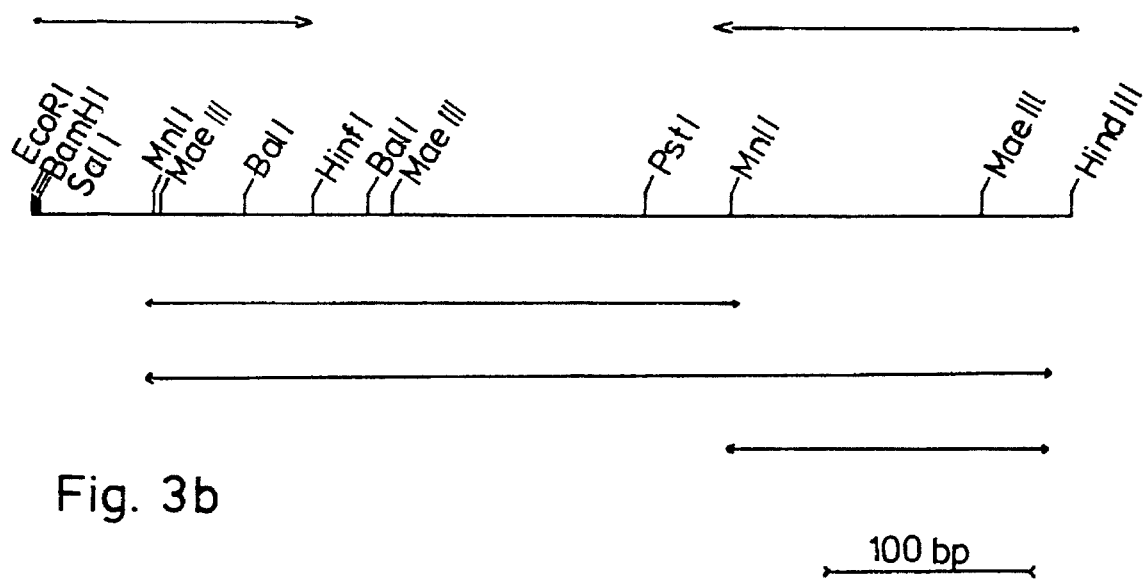
FIG. 3b shows the strategy for determining the nucleotide sequence of HLZ cDNA.

200 µg of pHL14-1 plasmid DNA was digested to completion with BamHI or HindIII restriction endonuclease, labelled at the 5' end with (gamma-$^{32}$P) ATP (Example 3b) and subsequently cleaved with a second endonuclease. The uniquely labelled DNA fragments were separated by polyplasmid pHL14-1) was combined with the longest 3' end of the HLZ insert (clone HL23, plasmid pHL 23)-Example 5b. The 3' end of HLZ DNA of pHL23 has the following sequence:

```
         PstI     10                 20              30              40
    5'   GACTGCAGTG         CTTTGCTGCA      AGATAACATC      GCTGATGCTG 50                 60              70              80
         TAGCTTGTGC         AAAGAGGGTT      GTCCGTGATC      CACAAGGCAT 90                100             110             120
         TAGAGCATGG         GTGGCATGGA      GAAATCGTTG      TCAAAACAGA 130                140             150    MaeIII   160
         GATGTCCGTC         AGTATGTTCA      AGGTTGTGGA      GTGTAACTCC 170                180             190             200
         AGAATTTTCC         TTCTTCAGCT      CATTTTGTCT      CTCTCACAAT 210                220    MaeIII   230             240
         TAAGGGAGTA         GGTTAAGTGA      AAGGTCACAT      ACCATTATTT 250                260
         CGGGGGGGGG         GGGGGGGGGG       3'
``` acrylamide or agarose gel electro-phoresis (FIG. 3). Labelled DNAs were recovered by electroelution and subjected to sequence analysis by the method of Maxam and Gilbert (26). The top arrows in FIG. 3b indicate the direction and extent of sequence analysis accomplished by this method; the asterisks indicate labelling sites.

The internal part of pHL14-1 cDNA was sequenced according to the method of Sanger (27). The BamHI - HindIII restriction fragment of pHL14-1 containing HLZ cDNA-was partially digested with MnlI restriction endonuclease, the ends were blunt-ended with Klenow polymerase according to the method of Maniatis et al. (28) and cloned into M13 Mp9 which was cut with SmaI. All DNA manipulations with M13 as well as sequencing were done exactly as described in the Amersham booklet "M13 cloning and sequencing handbook". The restriction fragments which have been cloned and sequenced by this method are shown in FIG. 3b (lower arrows). Only the positions of relevant restriction sites are indicated in the clone HL14-1. The presence of recognition sites for endonucleases MnlI, MaeIII and HinfI was confirmed experimentally.

Figure 4B:
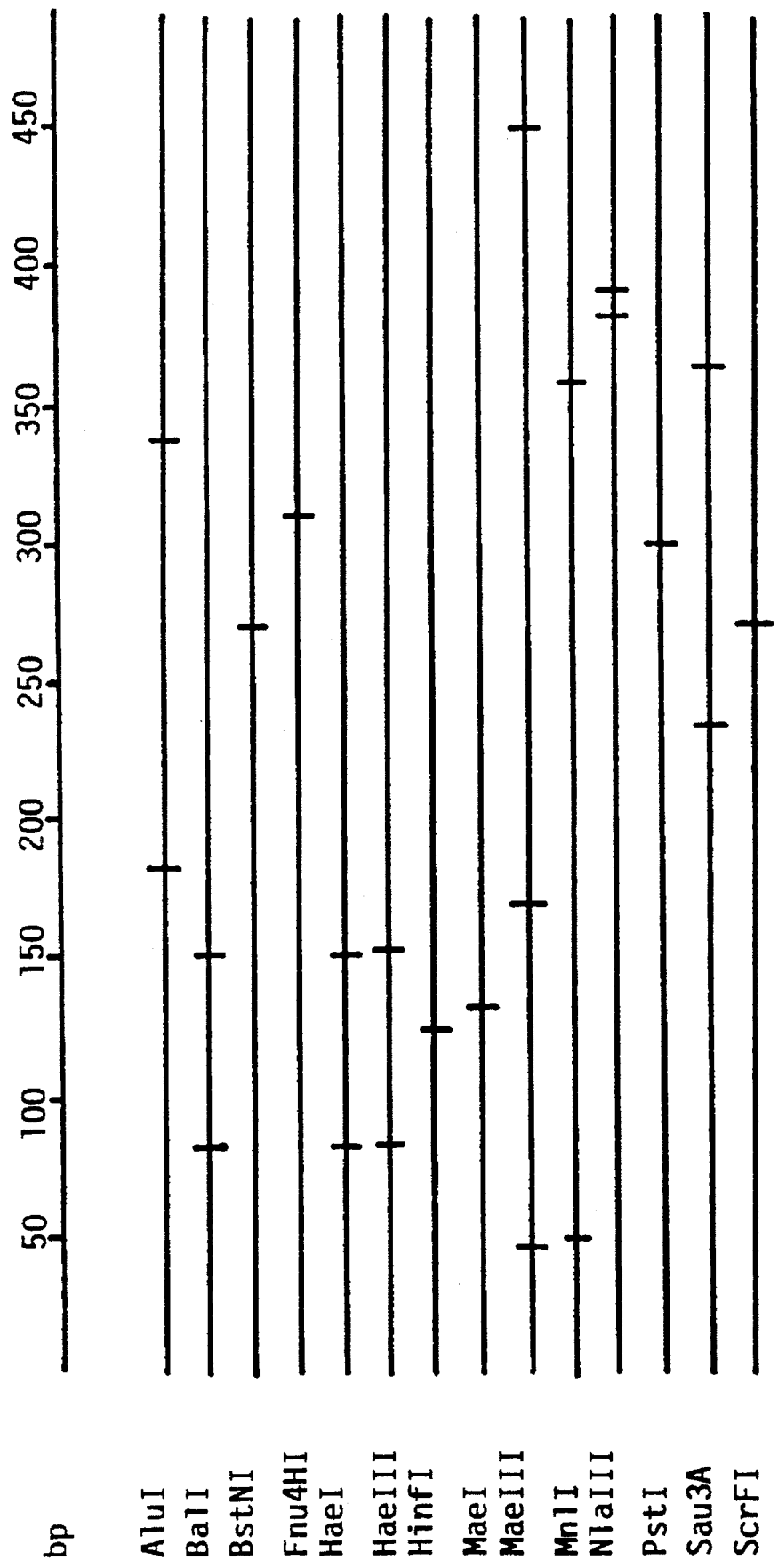
FIG. 4b shows the restriction map of the HLZ cDNA of clone HL 14-1
Figure 6:
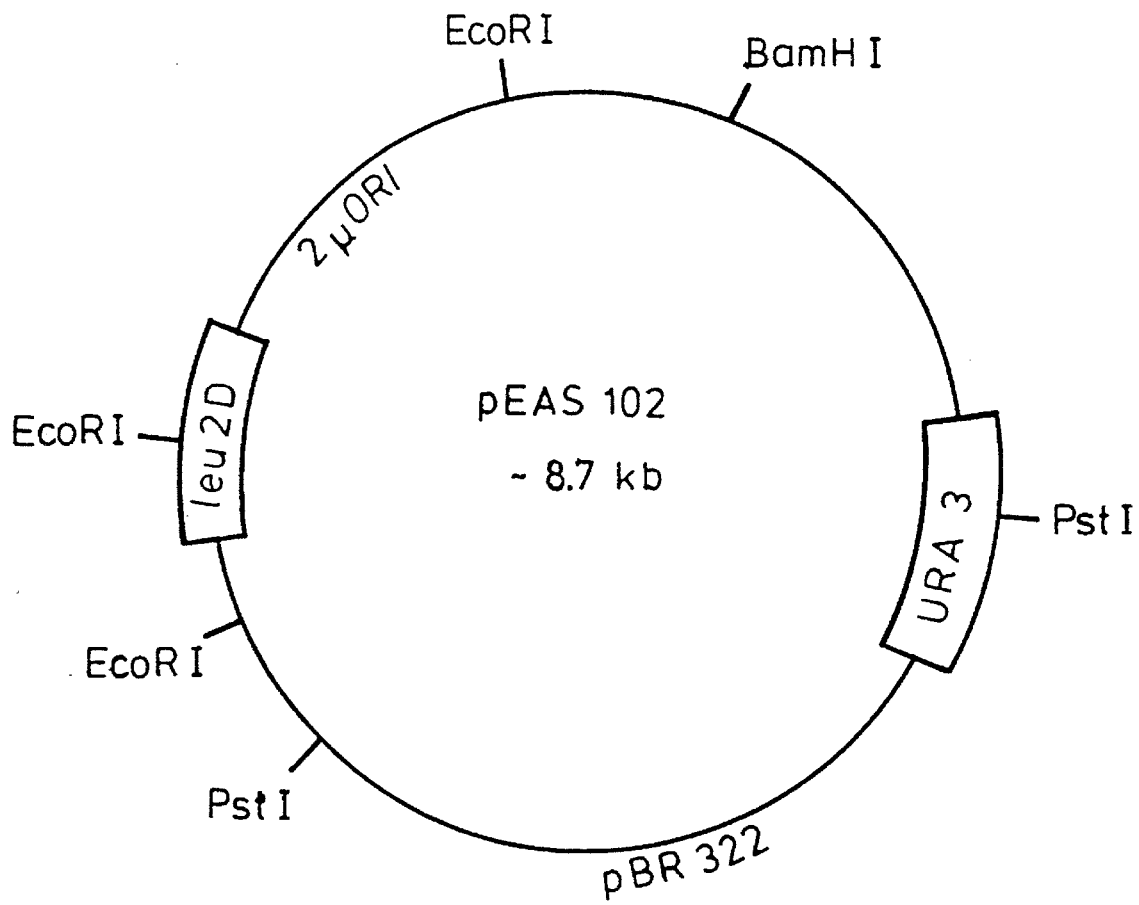
FIG. 6 shows the multicopy hybrid vector pEAS102 (for its construction and use see page 14 of the text)

The results of the DNA sequencing are given in FIG. 4. An open reading frame is found in the HLZ cDNA sequence upstream of nucleotide 20. Nucleotides 62-451 correspond precisely to the amino acid sequence for human lysozyme (FIG. 5) and are followed by the translation stop codon TAA. The nucleotides 20-61 coding for 14 mainly hydrophobic amino acids: 5' Ile Val Leu Gly Leu Val Leu Leu Ser Val Thr Val Gln Gly Lys Val etc. code for part of the HLZ leader or signal peptide similar to other secreted proteins (29). The amino acid composition of the splice junction of human pre-lysozyme is very similar to that of hen egg white lysozyme (Gln Gly Lys Val for human pre-lysozyme versus Leu Gly Lys Val for hen egg white lysozyme) (Weisman L. S. et al., J. Biol. Chem. 261, 2309–2313, 1986).

EXAMPLE 7

Construction of pHL14-23

To construct the expression plasmid in order to prepare HLZ the longest 5' end of the HLZ insert (clone HL14-1, The 5' end up to the PstI site (FIG. 4) corresponds to the DNA sequence of pHL 14-1.

About 1 µg of pHL23 was digested with PstI and HindIII at 36° C. (50 mM Tris HCl pH8.0, 1 mM MgCl$_2$, 50 mM NaCl) and separated in a 1% agarose gel. The PstI/HindIII fragment, 260 bp long, isolated from the agarose gel by the method of Dretzen, G. (Dretzen, G. et al. Anal. Biochem. 112, 295–298, 1981) contains the 3' end of the HLZ structural gene. This fragment (about 500 ng) was ligated in pHL 14-1 (about 50 ng) after the 190 bp PstI/HindIII fragment had been removed from pHL 14-1. The ligation of the DNA was carried out in a 20 µl mixture at 14° C. overnight in ligation buffer (66 mM Tris HCl pH7.6, 6.6 mM MgCl$_2$, 10 mM DDT, 1 mM rATP) and 1U T4 DNA ligase and the ligase mixture was used for transforming competent cells of E. coli HB101 by known methods (Maniatis, T. et al. Molecular Cloning, Cold Spring Harbor Press, S. 220, 1982).

EXAMPLE 8

Construction of an expression cassette under the control of the ADHI promoter a) Linking the ADHI promoter to the α-factor leader The starting material used was the pUC18 derivative pES103 which contains the ADHI promoter as a 1.5 kb long BamHI/XhoI fragment. Instead of pES103, YEp13 (ATCC 37 115) can also be used in the same way (Ammerer, G., Methods in Enzymology, 101, 192–201, 1983). Beside the XhoI site there is a PstI and a HindIII site, so that a 250 bp long HindIII/PstI fragment of the α-factor gene from pαF, which contains a large amount of the α-factor leader (FIG. 7), can be ligated between the HindIII and PstI site of pES103. The DNA sequence of the HindIII/PstI fragment with the α-factor leader has been published (Singh, A, et al., Nucleic Acid REs. 11 (12), 4049–63, 1983).

For this purpose 1 µg of pES103 and 5 µg of pαF were totally digested in 50 mM Tris HCl pH8.0, 10 mM MgCl$_2$, 50 mM NaCl at 36° C. with HindIII and PstI and ligated as described above (Example 7), using about 50 ng of pES103 (HindIII/PstI) and about 500 ng of pαF (HindIII/PstI). The resulting plasmid, transformed in *E. coli* HB101, with the correct orientation of the α-factor leader to the ADHI promoter was designated pWS205D. The missing 25 bp of α-factor leader sequence at the splice junction with the ADHI promoter, together with the ATG start codon, were replaced by a 40-mer oligonucleotide synthesised by the phosphotriester method (Efimov, V. A., et al., Nucleic Acid Res. 10, 6675–94, 1982). For this purpose, 1 µg of pWS205D was totally digested with XhoI and PstI in 50 mM Tris HCl, pH8.0, 10 mM MgCl$_2$, 50 mM NaCl at 36° C. The oligonucleotide

```
5'  TCGAGAAAAGAATGAGATTTCCTTCAATTTTTACTGCA      3'
3'          CTTTTCTTACTCTAAAGGAAGTTAAAAATG      5'
    XhoI                                     PstI
``` provided with XhoI and PstI ends was ligated with XhoI-PstI cut pWS205D: the oligonucleotides were taken up in a concentration of 10 pMol/ul of water, 5 ul portions of the solutions of the two DNA strands were combined, heated to 65° C. for 10 minutes and, after cooling to ambient temperature, 1 µl of this solution was used for the ligase reaction in ligase buffer and under the conditions described in Example 7. The resulting plasmid pWS209D thus contains the region about 1.5 kb long with the ADHI promoter and the complete α-factor leader up to the start of the coding region of the α-factor.

b) Linking the α-factor leader to the HLZ gene

Since the α-factor leader sequence in pWS209-D ends with a HindIII site and the HLZ gene in pHL14-23 is bounded at the 3' end by a HindIII site and at the 5' end by an SalI site, pH14-23 was totally digested with SalI in 6 mM Tris HCl pH8.0, 6 mM MgCl$_2$, 150 mM NaCl at 36° C. and the projecting ends were filled with klenow polymerase (total volume of 25 ul in ligase buffer as in Example 7, 0.5 µg of cut DNA, 100 µM each of dATP, dTTP, dCTP, dGTP, 1 U klenow polymerase, 30 mins at ambient temperature). The subsequent purification of the blunt-ended SalI digestion products was carried out in 1% agarose gel. Linker ligation was then carried out with a synthetic HindIII linker (new England BioLabs) (Maniatis, T. et al., Molecular Cloning, Cold Spring, Harbor Press, page 316, 1982). The linkers were taken up in a concentration of 1 µg/ul of water. The kinasing of the HindIII linker was carried out in a reaction mixture of 1 µl of 10× linker kinasing buffer (0.66M Tris HCl pH 7.9, 10 mM ATP, 10 mM spermidine, 0.1M MgCl$_2$, 150 mM DTT, 2 mg/ml BSA), 1 µl of linker, 6 µl of H$_2$O and 2 U T4 DNA kinase at 37° C. for 1 hour. The linker ligation with the kinased HindIII linker was carried out with about 0.5 µg/ul of the pHL14-23 treated with SalI and klenow polymerase in 10 ul of 1× linker kinasing buffer with 10 U T4 DNA ligase at 14° C. overnight. *E. coli* HB101 was transformed with the resulting plasmid pWS207D in which the HLZ gene is now flanked by two HindIII sites.

After HindIII digestion of 1 µg pWS207D (50 mM Tris HCl pH 8.0, 10 mM MgCl$_2$, 50 mM NaCl, 36° C.) the HLZ gene could now be ligated behind the α-factor leader as a HindIII fragment in HindIII cut pWS209D (5 ug). For the ligase reaction, after separation and isolation of the HindIII fragments in 1% agarose gel (Dretzen et al., see above) about 50 ng of pWS207D and about 500 ng of pWS209D are used in a 20 µl mixture consisting of ligation buffer (66 mM Tris HCl pH 7.6, 6.6 mM MgCl$_2$, 10 mM DTT, 1 mM rATP and 1 U T4 DNA ligase. The reaction is carried out overnight at 14° C. The resulting plasmid, containing the HLZ gene in the correct orientation relative to the α-factor leader or the ADHI promoter, was designated pWS215D.

c) Exact transition between the α-factor leader and the HLZ gene

In order to produce an exact N-terminus for the HLZ gene, it is essential that the protease cutting site which is responsible for the maturation of the α-factor is positioned precisely before the sequence for the first amino acid of the mature HLZ. Thus, the excess nucleotides (about 20 dG-dC pairs) originating from the construction of the cDNA and those nucleotides which code for the authentic HLZ leader sequence had to be eliminated.

Plasmid pWS215D was totally digested with PstI (50 mM Tris HCl pH 8.0, 10 mM MgCl$_2$, 50 mM NaCl, 36° C.) and a 500 bp long fragment which contains a large proportion of the α-factor leader and the 5' end of the HLZ gene, was isolated from a 1% agarose gel. (Dretzen et al, see above), according to Carter, P. et al. It was recloned in M13 amp18-am4 (Carter, P., Bedoulle, H., Winter, G., Nucleic Acid Res. 13, 4431–43, 1985) and transformed into *E. coli* strain TG1.

A recombinant phage with the desired orientation, A2, was used as the source of single stranded DNA for the in vitro mutagenesis. Template DNA was prepared as for dideoxy-sequencing (M13 cloning and sequencing handbook, Amersham International plc, Amersham UK). A 20-mer oligonucleotide EBI124, containing the desired transition between the α-factor leader and HLZ gene, and a 17-mer selection oligonucleotide EBI234, which corrects the amber mutation present in the M13 vector, were synthesised by the phosphotriester method (Efimov, V. A. et al., Nucleic. Acid Res. 10, 6675–94, 1982), purified by preparative polyacrylamide gel electrophoresis and used as a primer for the synthesis of the second DNA strand. The oligonucleotide mutagensis was carried out substantially according to the method of Zoller, M. J. and Smith, M. DNA 3, 479–488, 1984: 150 pmol of the selection oligonucleotide EBI234 having the sequence

5'AAGAGTCTGTCCATCAA 3' and 150 pmol of the mutagenic primer EBI124 having the sequence

5'GGATAAAAGAAAGGTCTTTG 3' were phosphorylated with 4 U T4 polynucleotide kinase (New England BioLabs) in 20 µl of 5 mM Tris HCl pH 8.0, 10 mM MgCl$_2$, 1 mM rATP, 5 mM DTT at 37° C. for 45 minutes and then heated for 10 minutes at 70° C. The kinased primers, 7.5 pmol of each, were hybridised with 0.5 pmol of template DNA in 10 µl of 10 mM Tris. HCl pH 8.0, 10 mM MgCl$_2$, 50 mM NaCl, by heating to 100° C. for 3 minutes and then cooling to ambient temperature over a period of 1 hour. The renatured mixture was chilled on ice, the volume was adjusted to 20 µl of 10 mM Tris HCl pH 8.0, 10 mM MgCl$_2$, 25 mM NaCl, 0.25 mM dNTP (dATP, dTTP, dCTP, dGTP), 0.25 mM rATP and the primer was extended with 1 U of the large fragment of DNA Polymerase I (BioLabs) in the presence of 10 U T4 DNA ligase (BioLabs). The reaction was carried out for 16 hours at 14° C. Small aliquots of the mixture, 0.1, 1.5 and 10 µl, were then used to transfect competent *E. coli* HB2154 cells (without suppressor), while the cell lawn was provided by HB2155 (Carter P., et al. Nucleic Acid Res. 13, 4431–4443, 1985).

84 of the 222 plaques resulting from the transfected DNA were transferred on to one LB-plate and grown up as colonies of infected bacteria for 16 hours at 37° C. A nitrocellulose blot was prepared and screened with the $^{32}$p labelled mutagenic oligonucleotide EBI124. The nitrocellulose filter was prewashed in 6× SSPE (0.9M NaCl, 0.06M NaH$_2$PO$_4$, 6 mM EDTA) for 5 min at room temperature, prehybridised in hybridisation buffer (6× SSPE, 1% Sarkosyl [Sigma], 100 µg/ml randomly cleaved tRNA) for 15 min at 37° C. and hybridised at room temperature (22° C.) for 16 hours in hybridisation buffer containing 0.4×10$^6$ cpm/ml of probe. The probe was 5' end labelled with ($\gamma$-$^{32}$p) ATP: 30 pmol of mutagenic primer, EBI124, Were phosphorylated with 4 U of T4 polynucleotide kinase (BioLabs) in 20 µl 50 mM Tris HCl pH 7.6, 10 mM MgCl$_2$, 10 mM DTT, 1 mM spermidine, 100 µg/ml BSA and 10 pmol ($\gamma$-$^{32}$p) ATP (5000 Ci/mmol, Amersham), at 37° C. for 45 min. The reaction mixture was then chromatographed on Biogel P-6DG (Biorad) in TE buffer (10 mM Tris HCl pH 7.5, 1 mM EDTA) to separate unincorporated ($\gamma$-$^{32}$p) ATP from the $^{32}$P-labelled oligonucleotide.

After hybridisation the filter was washed 3 times in 6× SSC (0.9M NaCl, 0.09M Na citrate) at room temperature for 5 min and once in prewarmed 6× SSC at 37, 47.5, 50 and 56° C. for 5 min and autoradiographed after each wash. Autoradiography after 56° C. (T$_D$+2° C.) revealed one clone, A2/25, hybridising strongly to the mutagenic oligonucleotide. The putative mutant phage was plaque purified, re-screened to identify pure mutant phage, and sequenced to verify the deletion.

Double stranded DNA from clone A2/25 was prepared as described by Yanisch-Perron et al. (Yanisch-Perron, C., Vieira, J., and Messing, J., Gene 33, 103–119, 1985) and was cleaved with PstI (about 5 µg in 50 mM Tris HCl pH 8.0, 10 mM MgCl$_2$, 50 mM NaCl, 36° C.). The 440 bp PstI fragment, which now contains the desired transition between the α-factor leader and the mature HLZ gene, was isolated from a 1% agarose gel as described (Dretzen et al, see above) and used for the ligations explained in more detail below (Examples 8e and 9d).

d) ADHII terminator and 3' end of the HLZ gene

The ADHII terminator (Beier, D. R., Young, E. T., Nature 300, 724–728, 1982; Russell, D. W. et al., J. Biol. Chem, 258, 2674–2682, 1983) was isolated from the plasmid pAS5 by digesting 5 µg of pAS5 with SphI/XbaI (6 mM Tris HCl pH 7.4, 6 mM MgCl$_2$, 150 mM NaCl, 1 mM DTT, 36° C.) and isolated from a 1% agarose gel as described. The DNA sequence of the ADHII terminator has been described by Russell, D. W. et al. (see above). The digestion of pUC18 (Vieira, J. Messing, J., Gene 19, 259–268, 1982; Yanisch-Perron et al. Gene 33, 103–119, 1985) was carried out with SphI and XbaI under the conditions specified above. Then about 50 ng of the digested vector and about 500 ng of the ADHII terminator (SphI/XbaI fragment) were ligated in a reaction mixture of 20 µl in ligation buffer (66 mM Tris HCl pH 7.6, 6.6 mM MgCl$_2$, 10 mM DTT 1 mM rATP) with 1 U T4 DNA ligase at 14° C. overnight. E. coli HB101 was transformed with the resulting plasmid pWS213D.

Since the HLZ DNA from pHL14-23 after the stop codon has further nucleotides of a non-coding region and a stretch of 20 dC-dG pairs originating from the preparation of the cDNA, these were removed. For this purpose, pHL14-23 was digested with MaeIII (20 mM Tris HCl pH 8.0, 6 mM MgCl$_2$, 350 mM NaCl, 1 mM DTT, 45° C.) and isolated (Dretzen et al. see above). The 280 bp long MaeIII-fragment obtained was cut exactly in the stop codon and contains the 3' end of the HLZ gene.

The projecting ends were filled with klenow polymerase by reacting about 0.5 µg of the DNA cut with MaeIII in a total volume of 25 µl of ligase buffer (see above) with 100 uM dATP, dTTP, dCTP, dGTP and 1 U klenow polymerase for 30 minutes at ambient temperature. About 1 ug of pWS213D was digested with SmaI (6 mM Tris HCl pH 8.0, 6 mM MgCl$_2$, 20 mM KCl)at 36° C. and the blunt ended MaeIII fragment of pHL14-23 (about 500 ng) was ligated in the SmaI site of pWS213D (about 50 ng) (conditions as described above).

The resulting plasmid with the correct orientation of the HLZ gene to the ADHII terminator was designated pWS235D. This plasmid contains the 3' end of the HLZ gene up to and including the stop codon and then the ADHII terminator. Between the HLZ gene and the ADHII terminator there are a BamHI and an XbaI cutting site which originate from the multi-cloning site of the plasmid pUC18. Since the BamHI site causes problems in subsequent constructions it was removed. For this purpose, pWS235D was cut with BamHI at 36° C. (6 mM Tris HCl pH 8.0, 6 mM MgCl$_2$, 150 mM NaCl, 1 mM DTT), the projecting ends were filled with klenow polymerase (see above) and an SalI linker was incorporated under the conditions described above (Example 8b). The plasmid formed was designated pW257D and E. coli HB101 was transformed therewith. The connecting sequence between the 3' end of the HLZ gene and the 5' end of the ADHII terminator runs as follows:

| 5'HLZ— | GTAAC | GGG | GGATC | GGTCGACC | GATCC | TCTAGA | — |
|---|---|---|---|---|---|---|---|
| ADHII-T.3' |  |  |  |  |  |  |  |
| — | CATTG | CCC | CCTAG | CCAGCTGG | CTAGG | AGATCT | — |
|  | 1 | 2 | 3 | 4 | 5 | 6 |  |

1 = 3' end of HLZ, digested with MaeIII and filled with klenow polymerase, with the stop codon TAA
2 = Remainder of the SmaI cloning site (pWS213D)
3 = Opened BamHI site filled with klenow polymerase
4 = SalI linker (New England BioLabs)
5 = Other end of the BamHI site of 3 (opened and filled with klenow polymerase)
6 = XbaI site and start of the ADHII terminator e) Construction of the expression cassette The plasmid pWS215D (approx. 1 ug) constructed in Example 8b was digested with PstI and HindIII (for conditions see Example 8a), whereby the entire HLZ gene and a large part of the α-factor leader were cut out with the resulting 4.2 kb fragment. Under the same conditions, pWS257D was digested with PstI and HindIII and the resulting fragment was ligated into the PstI/HindIII site with the ADHII terminator and the 3' end of the HLZ gene. The ligase reaction was as described above (Example 8d). In the resulting plasmid pWS218D, the 3'-end of the HLZ gene, which ends with the stop codon, and adjacent to it the ADHII terminator are situated directly at the start of the α-factor leader. For completion of the expression cassette a large part of the α-factor leader and the 5' end of the HLZ gene and the correct transition between these two elements are still missing. Therefore the mutaginised 440 bp long PstI fragment (about 500 ng) prepared in Example 8c was ligated into the PstI cutting site of pWS218D (about 50 ng) under the conditions described above. The plasmid with the correct orientation of the 440 bp long PstI fragment (5' end of the HLZ gene and large part of the α-factor leader (3' end)) relative to the ADHI promoter or the 3' end of the HLZ gene was designated pWS290D. The plasmid pWS290D thus contains all the elements described in the correct sequence and orientation relative to one another and the modified precise transitions between the individual elements: 1450 bp ADHI promoter, 260 bp α-factor leader (ends with a sequence which codes for a protease cutting site), 390 bp HLZ gene (begins with a lysine codon with an adjoining sequence for the mature HLZ protein and ends with the stop codon of the HLZ gene), 330 bp ADHII terminator.

f) Expression of HLZ in yeast

The expression cassette pWS290D (5 μg) was digested with HindIII and BamHI at 36° C. (50 mM TrisHCl pH 8.0, 10 mM MgCl$_2$, 50 mM NaCl) and ligated into the multicopy vector pJDB207 (1 μg) which had also been cut with HindIII and BamHI.

Both the expression cassette pWS290D (5 ng) and also the multicopy vector pJDB207 (1 μg) (Beggs, J. D., Gene cloning in yeast, in: Williamson, R. (Ed.), Genetic engineering, Vol.2, Academic Press, London 1981, 175–203; DSM-3181) were digested with HindIII and BamHI at 36° C. (50 mM TrisHCl pH 8.0, 10 mM MgCl$_2$, 50 mM NaCl). The prepared HindIII/BamHI fragment (about 500 ng) was ligated into the multicopy plasmid pJDB207 (about 50 ng) thus opened (20 μl of mixture with ligation buffer and under the conditions specified in Example 7, with 1 U T4 DNA ligase). Various heterothallic yeast strains of *Saccharomyces cerevisiae* were transformed with this plasmid 129/29 as follows (Beggs, J. D. *Nature* 275, 104–109, 1978): from a preliminary culture grown overnight in YPD (1% bacto yeast extract, 2% bacto peptone, 2% glucose), 10$^7$ cells/ml were inoculated into 50 ml of YPD and two generations were cultivated at 28° C. (generally for 3 hours). The preparation was centrifuged for 5 minutes at 5000 rpm, the cells were resuspended in 5 ml of SED (1M sorbitol, 25 mM EDTA, pH 8.0, 50 mM DTT) and slowly agitated at 30° C. for 10 minutes. The preparation was centrifuged for 5 minutes at 1600 rpm, resuspended in 5 ml of SCE (1M sorbitol, 0.1M Na$_3$ citrate, pH 5.8, 10 mM EDTA), 100 μl were taken and suspended in 2.9 ml of H$_2$O. The formation of spheroplasts was measured at 600 nm. Treatment with 50 μl of glusulase was then carried out with slow agitation at 28° C. After various times a further 100 μl of spheroplasts were taken, suspended in 2.9 ml of H$_2$O and the E$_{600}$ was determined. When the extinction at 600 nm had fallen to about. 30% of the initial value (usually after 20 to 30 minutes) the cells were centrifuged at 1600 rpm (bench centrifuge). The spheroplasts were washed once with 5 ml of CaS (1M sorbitol, 10 mM CaCl$_2$, 10 mM TrisHCl pH 7.5) slowly centrifuged again and taken up in 0.5 ml of CaS. Aliquot quantities of spheroplasts were taken, 1 μg of plasmid DNA (129/29) was added (in the case of larger volumes of DNA solution this must be adjusted to 1M sorbitol) and after leaving-to stand for 15 minutes at ambient temperature 1 ml of PEG (20% w/v PEG 4000, 10 mM CaCl$_2$, 10 mM TrisHCl pH 7.5, filtered sterile) was then added. The mixture was left to stand for 15 minutes at ambient temperature, centrifuged at 1600 rpm (bench centrifuge) the pellet was resuspended in 150 μl of SOS (1M sorbitol, 33% v/v YPD, 6.5 mM CaCl$_2$, 13.5 μg of the sterilised amino acid which had been selected for) and left to stand for 20 minutes at 30° C. This mixture was gently shaken in 3 ml of top agar which had been pre-cooled to 45° C. (1M sorbitol, 2.5% agar, 0.67% BYNB wo aa [Bacto yeast nitrogen base without amino acids], 2% glucose, 1% 100× amino acid mix), poured onto bottom agar plates (2% agar, 0.67% BYNB wo aa, 2% glucose, amino acid mix as for top agar) and cultivated for 2 to 4 days at 30° C. The 100× amino acid mix-leu contained 2 g/l of adenine sulphate, arginine, uracil, asparagine, glutamine, histidine, methionine, lysine, tyrosine, phenylalanine, valine, threonine, tryptophan. Transformed yeast strains (*Saccharomyces cerevisiae*) were cultivated on sc-leu (0.67% Bacto yeast nitrogen base without amino acids, 5% glucose, 1% 100× amino acid mix-leu) at 30° C.

The following Table shows the results of the lysozyme expression. The quantities of lysozyme were determined by specific antibody binding to lysozyme (Elisa-test)

| Transformant | Strain | Lysozyme (mg/l of culture) |
|---|---|---|
| 1/29 | WS21-5 | 0.4 |
| 1/31 | WS21-5 | 0.31 |
| 2/30 | WS21-3 | 0.89 |
| 2/31 | WS21-3 | 0.42 |
| 6/30 | WS21-1 | 1.0 |
| 6/31 | WS21-1 | 1.2 |

WS21-1 = a leu2 his3 trp1 pep4
WS21-3 = α leu2 his3 ura3 pep4
WS21-5 = α leu2 his3 trp1 arg1 pep4

EXAMPLE 9

Construction of an expression cassette under the control of the α-factor promoter Published studies (Bitter, G. A. et. al. Proc. Natl. Acad. Sci. USA 81, 5330–34, 1984; Brake, A. J. et al. Proc. Natl. Acad. Sci. USA 81. 4642–46, 1984) describe the insertion of heterologous genes between the HindIII and SalI site of the α-factor gene. The sequence between the EcoRI and the HindIII site acts as a promoter and a leader peptide whilst the sequence between SalI and EcoRI acts as a transcription terminator.

a. Cloning of the α-factor gene in a suitable vector

The α-factor gene was isolated from the pUC13 derivative pαF (5 μg) as an EcoRI fragment (100 mM TrisHCl pH 7.5, 5 mM MgCl$_2$, 50 mM NaCl, 1 mM DTT, 36° C.) and cloned into the vector V2. The vector V2 was constructed as follows: pUC18 was split with SamI and HindIII, the ends were filled with klenow polymerase as described above and the remaining amount of pUC18 was religated so that the resulting vector V2 had only three of the original ten cloning sites, namely EcoRI, SstI and KpnI. Thus, vector V2 no longer contains any HindIII or SalI site, with the result that the only cutting sites for these two enzymes are in the α-factor gene. The vector V2 (1 μg) was digested with EcoRI and about 500 ng of EcoRI-digested pαF were ligated into about 50 ng of EcoRI-digested V2 (ligase reaction as described in Example 7). The resulting plasmid pWS230D transformed in *E. coli* HB101 was used for further constructions (Example 9b, c). The PstI/BglII fragment from plasmid pWS230D (FIG. 14a) contains the promoter which is approximately 900 bp long. The PstI site next to it is about 25 bp inside the translated region. About 25 bp in front of the PstI site, which is adjacent to the four HindIII sites, and further upstream, there are the DNA regions required for the transcription of the α-factor gene. The leader sequence of the α-factor begins about 25 bp to the left of this second PstI site (ATG) and ends more or less exactly at the first of the four HindIII sites. The length is about 280 bp. The terminator is between the SalI and EcoRI site.

b) Joining the HLZ gene to the α-factor gene

So that the HLZ gene can be incorporated in the correct orientation relative to the α-factor promoter or terminator, the restriction cutting sites HindIII and SalI which flank pHL14-23 must be changed. To do this, about 5 µg of pHL14-23 was cut with SalI (6 mM TrisHCl pH 8.0, 6 mM MgCl$_2$, 150 mM NaCl, 36° C.) or HindIII (50 mM TrisHCl pH 8.0, 10 mM MgCl$_2$, 50 mM NaCl, 36° C.), the projecting ends were each filled with klenow polymerase (0.5 ug of cut DNA in a 25 µl reaction volume as in Example 8b) and the reaction mixture was purified in a 1% agarose gel. A HindIII linker (New England Biolabs) was ligated into the SalI site (pWS207D) and a SalI linker (New England Biolabs) was ligated into the HindIII site (pWS206D) (about 0.5 µg/µl of the DNA fragments in each case), as described in Example 8b) and transformed in E. coli HB101. The resulting plasmids pWS206D and pWS207D (approx. 5 µg of each) were cut with EcoRI and PstI (50 mM TrisHCl pH 8.0, 10 mM MgCl$_2$, 50 mM NaCl, 36° C.) and ligated to one another under the conditions of the ligase reaction described above (Example 7), to obtain plasmid pWS208D.

Here again, the 3' end of the HLZ gene described in Example 8d has the problem that there are additional nucleotides after the stop codon. For this reason the 3' end of the HLZ gene was shortened as follows to the stop codon: plasmid pWS257D (construction of Example 8d) contains the 3' end of the HLZ gene up to the stop codon, followed by a SalI site and the ADHII terminator, which is irrelevant to this construction. The plasmids pWS208D and pWS257D were totally digested with SalI and PstI (PstI in 50 mM TrisHCl pH 8.0, 10 mM MgCl$_2$, 50 mM NaCl, 36° C.; 1 hour, then the NaCl concentration is increased to 150 mM and SalI is added) and purified in a 1% agarose and isolated (Dretzen et al, see above). The SalI/PstI fragment of pWS257D which contains the 3' end of the HLZ gene replaces the SalI/PstI fragment of pWS208D, the fragment of pWS257D (about 500 ng) being ligated into the SalI/PstI site of pWS208D (about 50 ng) as described above. The resulting plasmid pWS212D now contains the complete HLZ gene as a HindIII/SalI fragment, whilst the HLZ gene at the 3' end terminates with the stop codon. The plasmids pWS212D and pWS230D (Example 9a) were totally digested with HindIII and SalI (HindIII in 50 mM TrisHCl pH 8.0, 10 mM MgCl$_2$, 50 mM NaCl, 36° C., 1 hour, then the NaCl concentration is increased to 150 mM and SalI is added), and the HLZ gene cut from pWS212D is ligated, as a HindIII/SalI fragment (about 500 ng) (isolated from a 1% agarose gel as described above), into the vector (approx. 50 ng) which has been opened with HindIII/SalI (ligase reaction as described in Example 7). In the resulting plasmid pWS231D the HLZ gene is now in the correct orientation relative to the α-factor promoter and terminator.

c) Removal of a PstI site from the α-factor gene

The α-factor gene contains 2 PstI sites. The one not located in the coding region is a major obstacle to further construction and therefore it was removed by the following procedure: plasmid pWS230D (for construction see Example 9a) was partially cut with PstI by digesting 10 ug of pWS230D in 50 mM of TrisHCl pH 8.0, 10 mM MgCl$_2$, 50 mM NaCl with 10 U PstI for 10 minutes at 36° C. Those fragments which contain precisely one cut (fragments B and C in FIG. 14a) were isolated from a 1% agarose gel. In order to digest away the 3' projecting ends with Mung Bean Nuclease, approximately 1 ug of the resulting linearised DNA of pWS230D was taken up in 13 µl of H$_2$O and 2 µl of 10 mM ZnCl$_2$, 1 µl 4M NaCl, 2 ul 0.3M sodium acetate pH 4.75, 2 µl of Mung Bean Nuclease (300 U, Pharmacia) were added. This mixture was left to stand for 15 minutes at ambient temperature and then applied directly to a 1% agarose gel and the fragments were isolated from the gel (Dretzen et al., see above). Then fragments B and C were religated (conditions as specified in Example 7), whereby the PstI site which had been cut during the partial digestion was destroyed and the one which had not been cut was retained. In this way it was possible to isolate a plasmid in which the desired PstI site no longer appeared but the other was retained (C'). Both this plasmid (C') and also pWS231D were totally digested with PstI and BglII (50 mM TrisHCl pH 8.0, 10 mM MgCl$_2$, 50 mM NaCl, 36° C.). The isolated C2 fragment (850 bp) of C' (approx. 500 ng) was ligated into PstI/BglII-digested pWS231D (about 50 ng) (ligase reaction as described in Example 7), so that plasmid pWS294D was obtained. This plasmid pWS294D now contains an α-factor gene with a PstI site into which the 3' end of the HLZ gene is inserted in the correct orientation.

d) Construction of the expression cassette

Plasmid pWS294D contains the α-factor promoter and the start of the α-factor peptide up to the PstI cutting site (approx. 20 bp leader peptide) and after that the 3' end of the HLZ gene from the PstI site to the stop codon. The complete expression cassette is still lacking the 3' end of the α-factor leader, the 5' end of the HLZ gene and the correct transition between these two elements. Plasmid pWS294D (approx. 1 µg) was totally digested with PstI (50 mM TrisHCl pH 8.0, 10 mM MgCl$_2$, 50 mM NaCl, 36° C.) and the mutagenised 440 bp PstI fragment from plasmid A2/25 (Example 8c) (about 500 ng) was ligated into the PstI site of pWS294D as in Example 8e. The resulting plasmid pWS296D contains the expression cassette consisting of the 900 bp promoter sequence of the α-factor gene, 260 bp α-factor leader (identical to the length of sequence described in Example 8e), 390 bp HLZ gene (identical to the length of sequence described in Example 8e) and 290 bp of α-factor terminator.

The invention now being fully described, it will be apparent to one of ordinary skill in the art that many changes and modifications can be made thereto without departing from the spirit or scope of the invention as set forth herein.

Bibliography

1. Phillips, D. C. Sci. Am. 215: 78–90 (1966)
2. Fleming, A. Proc. Roy. Soc. SerB93: 306–307 (1922)
3. Biggar, W. D. and Sturgess, J. M. Infect Immunol. 16: 974–982 (1977)
4. Thacore, M. and Willet, H. P. Am. Rev. Resp. Dis. 93: 786–790 (1966)
5. Klockars, M. I. and Roberts, P. Acta Haematol 55: 289–292 (1976)
6. Iacono, V. J., Mackay, B. J., DiRienzo, S. and Pollok, J. J. Infect. Immunol. 29: 623–632 (1980)
7. Jolles, P. Biomedicine 25: 275–276 (1976) Ossermann, E. F. Adv. Pathobiol 4: 98–102 (1976)
9. Jolles, P., Sternberg, M., Mathe, G. Isr. J. Med. Sci. I: 445–447 (1965)
10. Ossermann, E. F. and Lawlor, D. P. J. Exp. Med. 124: 921–952 (1966)
11. Sippel, A. E., Land, H., Lindenmair, W., NguyenHum, M. C., Wurtz, T., Timmis, K. N., Giesecke, K. and Sch ütz, G. Nucl. Acid Res. 5: 3275–3294 (1978)
12. Baldacci, P., Royal, A., Cami, B., Perrin, F., Krust, A., Garapin, A. and Kourilsky, P. Nucl. Acid Res. 6: 2667–2681 (1979)

13. Jung, A., Sippel, A. E., Grez, M. and Schütz, G. Proc. Nat. Acad. Sci. USA 77: 5759–5763 (1980)
14. Owen, J. E., Schultz, D. W., Taylor, A. and Smith, G. R. J. Mol. Biol. 165: 229–248 (1983)
15. Gubler, U. and Hoffmann, B. J. Gene 25: 263–269 (1983)
16. Ralph P., Moore M. A. S. and Nillson K. J. Exp. Medicine 143: 1528–1533 (1976)
17. Gold, L. M. and Schweiger, M. Methods in Enzymology, Vol. XX, Part C pp. 537–542, Ed. K. Moldave, L. Grossman, Academic Press, New York and London, 1971.
18. Vieira, J. and Messing, J. Gene 19: 259–268 (1982)
19. Peacock, S. L., McIver, C. M. and Monahan, J. J. Biochim, Biophys. Acta 655: 243–250 (1981)
20. Alvarado-Urbina, G., Sathe, G. M., Liv, W. C., Gillen, M. F., Duck, P. D., Bender, R. and Ogilivie, K. K. Science 214: 270–274 (1981)
21. Jolles, J. and Jolles, P. Helv. Chim. Acta 54: 2668–2675 (19 71)
22. Canfield, R. E., Kammermann, S., Sobel, J. H. and Morgan, F. J. Nature New Biol. 232: 16–17 (1971)
23. Jolles, P. and Jolles, J. Mol. Cell. Biochem. 63: 165–189 (1984)
24. Lee, C. D. and Luse, D. C. Focus 4: 1–3 (1982)
25. Birnboim, H. C. and Doly, J. Nucleic Acid Res. 7: 1513–1523 (1979)
26. Maxam, A. M. and Gilbert, W. Methods Enzymol 65: 498–560 (1980)
27. Sanger, F., Nicklen, S. and Coulson, A. R. Proc. Natl. Acad. Sci USA 74: 5463–5467 (1977)
28. Maniatis, T. Molecular cloning A Laboratory Manual. Cold Spring Harbor Laboratory (1982)
29. Lingappa, V. R. and Biobel, G. Recent. Prog. Horm. Res. 36: 451–476 (1980)

We claim:

1. A purified and isolated recombinant DNA molecule coding for human lysozyme, wherein said DNA molecule has the following sequence:

5' AAG GTC TTT GAA AGG TGT GAG TTG GCC AGA

ACT CTG AAA AGA TTG GGA

ATG GAT GGC TAC AGG GGA ATC AGC CTA GCA AAC

TGG ATG TGT TTG GCC

AAA TGG GAG AGT GGT TAC AAC ACA CGA GCT ACA

AAC TAC AAT GCT GGA

GAC AGA AGC ACT GAT TAT GGG ATA TTT CAG ATC

AAT AGC CGC TAC TGG

TGT AAT GAT GGC AAA ACC CCA GGA GCA GGT AAT

GCC TGT CAT TTA TCC

TGC AGT GCT TTG CTG CAA GAT AAC ATC GCT GAT

GCT GTA GCT TGT GCA

AAG AGG GTT GTC CGT GAT CCA CAA GGC ATT AGA

GCA TGG GTG GCA TGG

AGA AAT CGT TGT CAA AAC AGA GAT GTC CGT CAG

TAT GTT CAA GGT TGT

GGA GTG

2. The purified and isolated recombinant DNA molecule of claim 1, further comprising a stop codon after said molecule sequence.

3. A purified and isolated recombinant DNA molecule encoding human lysozyme and the human lysozyme leader or signal peptide, wherein said DNA molecule has the following sequence:

5' ATTGTTCTGGGGCTTGTCCTCCTTTCTGTTACGGTTCAAGGCAAGGTCTTTGAAAGGTGTGAGTTGGC
CAGAACTCTGAAAAGATTGGGAATGGATGGCTACAGGGGAATCAGCCTAGCAAACTGGATGTGTTTGG
CCAAATGGGAGAGTGGTTACAACACACGAGCTACAAACTACAATGCTGGAGACAGAAGCACTGATTAT
GGGATATTTCAGATCAATAGCCGCTACTGGTGTAATGATGGCAAAACCCCAGGAGCAGTTAATGCCTG
TCATTTATCCTGCAGTGCTTTGCTGCAAGATAACATCGCTGATGCTGTAGCTTGTGCAAAGAGGGTTG
TCCGTGATCCACAAGGCATTAGAGCATGGGTGGCATGGAGAAATCGTTGTCAAAACAGAGATGTCCGT
CAGTATGTTCAAGGTTGTGGAGTGTAACTCCAGAATTTTCCTTCTTCAGCTCATTTTGTCTCTCTCA
CAATTAAGGGAGTAGGTTAAGTGAAAGGTCACATACCATTATTTC.

4. An expression vector comprising the isolated and purified recombinant DNA molecule of claim 1.

5. The expression vector of claim 4, comprising in order an ADHI promotor, an alpha-factor leader, said isolated and purified recombinant DNA molecule and an ADHII terminator.

6. The expression vector of claim 4, comprising in order an alpha-factor promotor, an alpha-factor leader, said isolated and purified recombinant DNA molecule and an alpha-factor terminator.

7. The expression vector of claim 4 which is yeast-specific.

8. An expression vector comprising the isolated and purified recombinant DNA molecule of claim 3.

9. The expression vector of claim 8, which is capable of producing mature human lysozyme in a form secretable by a host.

10. The expression vector of claim 8 which is yeast-specific.

11. A recombinant plasmid comprising a nucleotide insert which is the isolated and purified recombinant DNA molecule of claim 1.

12. The recombinant plasmid of claim 11, which is capable of replication and expression in a host.

13. The recombinant plasmid of claim 11, which is replicable in prokaryotes.

14. The recombinant plasmid of claim 11, which is replicable in eukaryotes.

15. The recombinant plasmid of claim 11, wherein said nucleotide insert is positioned within the PstI cutting site of plasmid pUC 9.

16. The recombinant plasmid of claim 11, which is pHL2, pHL8, pHL14-1, pHL21, pHL23, pHL14-23 or pHL35.

17. The recombinant plasmid of claim 11 which comprises an additional insert selected from the group consisting of a promoter, a leader sequence, or a terminator which is functionally connected to said insert comprising said purified and isolated DNA sequence coding for human lysozyme.

18. A recombinant plasmid comprising a nucleotide insert which is the isolated and purified recombinant DNA molecule of claim 3.

19. The recombinant plasmid of claim 18, which is capable of replication and expression in a host.

20. The recombinant plasmid of claim 18, which is replicable in prokaryotes.

21. The recombinant plasmid of claim 18, which is replicable in eukaryotes.

22. The recombinant plasmid of claim 18, wherein said insert is positioned within the PstI cutting site of plasmid pUC 9.

23. A transformed host comprising the recombinant DNA molecule of claim 1.

24. The transformed host of claim 23 which is a prokaryote.

25. The transformed host of claim 23 which is a eukaryote.

26. The transformed host of claim 23, wherein said recombinant DNA molecule is comprised by a vector capable of replication in said host.

27. The transformed host of claim 23, which expresses human lysozyme.

28. The transformed host of claim 23 which is *E. coli*.

29. The transformed host of claim 28 which is *E. coli* RRI.

30. The transformed host of claim 23 which is yeast.

31. The transformed host of claim 30 which is *Saccharomyces cerevisiae*.

32. The transformed host of claim 23 which is a mammalian cell line.

33. A transformed host comprising the recombinant DNA molecule of claim 3.

34. The transformed host of claim 33 which is a prokaryote.

35. The transformed host of claim 33 which is a eukaryote.

36. The transformed host of claim 35, wherein said recombinant DNA molecule is contained by a vector capable of replication in said host.

37. The transformed host of claim 33, which expresses human lysozyme.

38. The transformed host of claim 33 which is *E. coli*.

39. The transformed host of claim 38 which is *E. coli* RRI.

40. The transformed host of claim 33 which is yeast.

41. The transformed host of claim 40 which is *Saccharomyces cerevisiae*.

42. The transformed host of claim 33 which is a mammalian cell line.

43. A method of preparing mature human lysozyme, comprising:

(a) preparing the purified and isolated recombinant DNA molecule of claim 1;

(b) transforming a cellular host with said purified and isolated recombinant DNA molecule;

(c) culturing said host; and (d) collecting said mature HLZ.

44. The method of claim 43, wherein said cellular host is yeast.

45. A method of preparing mature human lysozyme, comprising:

(a) preparing the purified and isolated recombinant DNA molecule of claim 3;

(b) transforming a cellular host with said purified and isolated recombinant DNA molecule;

(c) culturing said host; and (d) collecting said mature human lysozyme.

46. The method of claim 45, wherein said cellular host is yeast.

\* \* \* \* \*

UNITED STATES PATENT AND TRADEMARK OFFICE
CERTIFICATE OF CORRECTION

PATENT NO. : 5,618,712

DATED : April 8, 1997

INVENTOR(S): Sledziewski *et al.*

It is certified that an error appears in the above-identified patent and that said Letters Patent is hereby corrected as shown below.

In claim 1, column 25, at line 66, delete "GGT" and insert therein --GTT--.

In claim 2, column 26, at line 21, delete "molecule" and insert therein --nucleotide--.

In claim 43, column 28, at line 26, delete "HLZ" and insert therein --human lysozyme--.

Signed and Sealed this

Twelfth Day of August, 1997

Attest:

BRUCE LEHMAN

Attesting Officer

Commissioner of Patents and Trademarks